United States Patent
Kammafoo et al.

(10) Patent No.: US 10,647,641 B2
(45) Date of Patent: May 12, 2020

(54) PROCESS FOR THE SEPARATION OF ETHYLBENZENE FROM OTHER $C_8$ AROMATIC COMPOUNDS

(71) Applicants: SCG Chemicals Co., Ltd., Bangkok (TH); Sulzer GTC Technology US Inc., Wilmington, DE (US)

(72) Inventors: Alisa Kammafoo, Rayong (TH); Attapong Thirasak, Rayong (TH); Zhongyi Ding, Katy, TX (US)

(73) Assignees: SCG Chemicals Co., Ltd., Bangkok (TH); Sulzer GTC Technology US Inc., Wilmington, DE (US)

( * ) Notice: Subject to any disclaimer, the term of this patent is extended or adjusted under 35 U.S.C. 154(b) by 0 days.

(21) Appl. No.: 16/516,656

(22) Filed: Jul. 19, 2019

(65) Prior Publication Data

US 2020/0024217 A1 Jan. 23, 2020

Related U.S. Application Data (60) Provisional application No. 62/701,059, filed on Jul. 20, 2018.

(51) Int. Cl.
| | |
|---|---|
| *C07C 7/08* | (2006.01) |
| *C07C 15/073* | (2006.01) |
| *B01D 3/14* | (2006.01) |
| *B01D 3/40* | (2006.01) |

(52) U.S. Cl.
CPC ............. *C07C 7/08* (2013.01); *B01D 3/143* (2013.01); *B01D 3/40* (2013.01); *C07C 15/073* (2013.01); *B01D 2256/24* (2013.01); *B01D 2257/40* (2013.01)

(58) Field of Classification Search
CPC .... C07C 7/08; C07C 7/10; C07C 7/11; C07C 7/005; B01D 3/40; B01D 2256/24; B01D 2257/40; B01D 3/143; B01D 71/021
See application file for complete search history.

(56) References Cited

U.S. PATENT DOCUMENTS

| | | | |
|---|---|---|---|
| 3,105,017 A | 9/1963 | Amir et al. | |
| 3,144,476 A * | 8/1964 | Haken | C07C 201/16 558/343 |
| 3,584,068 A | 6/1971 | Jackson et al. | |
| 3,624,172 A | 11/1971 | Adams | |
| 3,702,347 A | 11/1972 | Adams | |
| 3,856,871 A | 12/1974 | Haag et al. | |
| 4,101,596 A | 7/1978 | Mitchell et al. | |
| 4,299,668 A | 11/1981 | Berg | |
| 4,435,608 A | 3/1984 | Koetsier et al. | |
| 5,329,061 A | 7/1994 | Swift | |
| 5,397,441 A | 3/1995 | Berg | |
| 5,495,061 A | 2/1996 | Kulprathinpanja | |
| 5,948,950 A | 9/1999 | Hotier et al. | |
| 2002/0082462 A1 | 6/2002 | Ferraro et al. | |
| 2017/0247303 A1 * | 8/2017 | Thirasak | C08K 3/16 |

FOREIGN PATENT DOCUMENTS

| | | |
|---|---|---|
| GB | 1198592 | 7/1970 |
| WO | 2015142454 A1 | 9/2015 |
| WO | 2016036326 A1 | 3/2016 |
| WO | 2016036388 A1 | 3/2016 |
| WO | 2016036392 A1 | 3/2016 |
| WO | 2017105617 A1 | 6/2017 |

\* cited by examiner

*Primary Examiner* — Sharon Pregler
(74) *Attorney, Agent, or Firm* — Banner & Witcoff, Ltd.

(57) ABSTRACT

Extractive agent compounds are disclosed, with exemplary compounds having Formula (I):

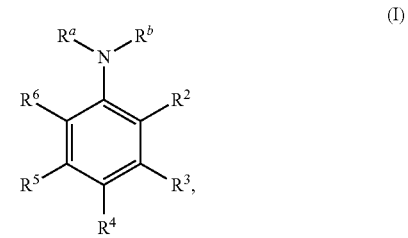

wherein $R^a$ and $R^b$ are independently selected from the group consisting of an oxygen radical, a hydrogen radical, and a hydrocarbyl radical having from about 1 to about 20 carbon atoms, and wherein $R^2$-$R^6$ are independently selected from the group consisting of halo, a hydrogen radical, and a hydrocarbyl radical having from about 1 to about 20 carbon atoms, and further wherein at least two of $R^2$-$R^6$ are halo. Also disclosed are extractive distillation processes, comprising distilling a liquid mixture comprising ethylbenzene, a further $C_8$ aromatic compound, and an extractive agent compound as described herein. The extractive agent contributes to improved separability of ethylbenzene from the further $C_8$ aromatic compound. The separability may be quantified in terms of increasing relative volatility of ethylbenzene to the further $C_8$ aromatic compound or may alternatively be quantified in terms of a competitive factor, D, as described herein.

20 Claims, 5 Drawing Sheets

PROCESS FOR THE SEPARATION OF ETHYLBENZENE FROM OTHER $C_8$ AROMATIC COMPOUNDS

CROSS-REFERENCE TO RELATED APPLICATIONS

This application claims priority to U.S. provisional application No. 62/701,059, filed Jul. 20, 2018, which is incorporated by reference in its entirety.

FIELD OF THE INVENTION

The present invention relates to an extractive distillation process for separation of ethylbenzene from a liquid mixture comprising ethylbenzene and at least one further $C_8$ aromatic compound, such as a xylene isomer, using an extractive agent to improve the separation.

BACKGROUND OF THE INVENTION

Separation of compounds having close boiling points usually requires a more complicated process, relative to conventional distillation methods. Extractive distillation is one technique developed for this purpose, which has been applied commercially and is becoming increasingly important as a separation method, particularly in the refining and petrochemical industries. A common characteristic of extractive distillation methods is the use of a heavy solvent, i.e., a high boiling point, extractive agent that is added to the mixture of the compounds to be separated. This extractive agent functions to increase the relative volatility of these compounds. Relative volatility provides an indication of the degree of their separability (ease of separation) by distillation from a liquid mixture of these compounds. In addition to altering the relative volatility, an effective extractive agent should also itself be easily separated from the distillation products. Thus, a significant difference in boiling point between the extractive agent and the compounds to be separated is desirable. The extractive agent plays an important role in the design of extractive distillation processes. Therefore, the selection of a suitable extractive agent is essential to ensuring the effective and economical design of an extractive distillation process.

Ethylbenzene is a hydrocarbon compound with high commercial utilization and value. A major use is for the production of styrene, which in turn serves as an intermediate in the manufacture of polystyrene. Ethylbenzene can be synthesized from the reaction of benzene and ethylene, or alternatively it can be recovered from an impure hydrocarbon mixture. For example, impure mixtures containing ethylbenzene are commonly produced as by-products of various petrochemical processes. Impure hydrocarbon mixtures containing ethylbenzene normally also contain other hydrocarbons, most notably other $C_8$ aromatic hydrocarbons (e.g., xylenes) having boiling points close to that of ethylbenzene.

Examples of impure ethylbenzene-containing mixtures are obtained from naphtha cracker effluents, in which pyrolysis gasoline streams are generated. It is desirable to extract valuable aromatic compounds, and mixtures of compounds, including benzene, toluene, ethylbenzene, and xylene from pyrolysis gasoline for further utilization. Benzene and toluene can be conveniently separated with known techniques, leaving a mixed $C_8$ hydrocarbon stream, comprising ethylbenzene in combination with xylenes. Such mixtures typically contain more than 60 wt-% ethylbenzene ("high ethylbenzene"), with most or all of the remainder being mixed xylenes that co-boil with each other and with ethylbenzene, rendering these components difficult to separate by conventional distillation.

Other impure ethylbenzene-containing mixtures are those used in processes for the production of para-xylene, in which a mixed $C_8$ hydrocarbon stream is separated from such mixture, for example a reformate stream that is a feed to a xylene column. This mixed $C_8$ hydrocarbon stream is then further separated, for example using known simulated moving bed processes employing a suitable adsorbent, into a para-xylene rich stream (e.g., recovered as a para-xylene rich product) and a para-xylene lean stream (or para-xylene depleted effluent). The para-xylene lean stream generally comprises meta-xylene, ortho-xylene, and minor amount of ethylbenzene, generally not exceeding 20 wt-% ("low ethylbenzene"). In order to increase the yield of para-xylene, the para-xylene lean stream is subsequently processed in a catalytic conversion step to dealkylate ethylbenzene. The dealkylated products are separated from the effluent obtained from this step, and the remaining stream, substantially comprising meta-xylene and ortho-xylene, is isomerized to increase the overall yield of the desired para-xylene isomer. This para-xylene enriched isomerate (or xylene-equilibrated isomerate, to the extent that para-xylene concentration is increased in the direction of its equilibrium concentration with the other xylene isomers) is then generally recycled to the xylene column.

Various attempts have been made to facilitate the separation of hydrocarbons from impure mixtures. Examples of these are described in GB 1,198,592; U.S. Pat. Nos. 3,105,017; 5,397,441; 4,299,668; WO 2016/036326; WO 2016/036388; and WO 2016/036392, which disclose the use of various operating conditions and/or extractive agents for this purpose. However, the proposed solutions generally involve one or more of high energy consumption, complex process flow schemes, the use of toxic agents, and/or other parameters that are generally undesirable. Accordingly, there remains a need in the art for extractive distillation processes that overcome various drawbacks associated with conventional techniques.

SUMMARY

Aspects of the invention are associated with the discovery of improved processes for the separation of ethylbenzene from a hydrocarbon component comprising ethylbenzene and at least one other $C_8$ aromatic compound. To perform extractive distillation, the hydrocarbon component may be combined with one or more extractive agent compound(s) as described herein, to provide a liquid mixture. The extractive agent compound effectively contributes to the desired separation, by increasing the relative volatility of ethylbenzene to the $C_8$ aromatic compound. Moreover, the extractive agent compound is itself easily separated from a distillate (e.g., recovered as a bottoms fraction of the extractive distillation) that is enriched in both the $C_8$ aromatic compound and the extractive agent compound, relative to the starting mixture. This allows for the convenient reuse (recycle) of the extractive agent compound, for example in a continuous extractive distillation process.

Other aspects are associated with the surprising discovery of a class of extractive agent compounds that are particularly useful and provide important advantages in extractive distillation, especially in the separation of ethylbenzene from a further (or other) $C_8$ aromatic compound. Representative extractive agent compounds include a carbocyclic or heterocyclic ring structure, the ring structure being substituted with at least one $NR^aR^b$-group radical and at least two halo radicals. $R^a$ and $R^b$ are independently selected from the group consisting of an oxygen radical, a hydrogen radical, and a hydrocarbyl radical having from about 1 to about 20 carbon atoms.

Accordingly, embodiments of the invention are directed to extractive distillation processes, comprising distilling a liquid mixture comprising ethylbenzene, a further $C_8$ aromatic compound, and an extractive agent compound as described herein. Advantageously, the extractive agent contributes to improved efficiency, or separability of ethylbenzene from the further $C_8$ aromatic compound. Improved separability may be quantified in terms of increasing relative volatility of ethylbenzene to the further $C_8$ aromatic compound, for example compared to a reference distillation performed with all parameters (e.g., temperature, pressure, and normalized composition that discounts the extractive agent compound(s)) being the same except for the absence of the extractive agent compound. Improved separability may alternatively be quantified in terms of a competitive factor, D, which is associated with the differing affinities of the extractive agent compound for the different compounds to be separated, as described and defined herein, of greater than 1. In this regard, those skilled in the art will appreciate, in view of the present disclosure, that even small increases in the relative volatility of ethylbenzene and/or the competitive factor provide substantial reductions in capital and/or energy requirements to achieve a given separation by distillation. These capital requirements are associated with the column height and separation stage requirements, and these energy requirements are associated with column reboiler and condenser duties.

Further advantages associated with extractive distillation processes described herein may include the ease of separation of the extractive agent compound, downstream of the extractive distillation, allowing for its continuous or intermittent recovery and/or reuse (e.g., recycle back to the extractive distillation), thereby reducing raw material consumption. Yet other advantages may be associated with the flexibility of extractive agent compounds described herein, for use with improved efficiency over a wide range of ethylbenzene concentrations in liquid mixtures that are subjected to extractive distillation. For example, representative hydrocarbon components of such liquid mixtures include both "high ethylbenzene" streams and "low ethylbenzene" streams as described herein. According to a particular embodiment, an extractive distillation process as described herein may provide an attractive alternative to performing catalytic conversion (e.g., dealkylation) to remove ethylbenzene from a reformate stream, a mixed $C_8$ hydrocarbon stream, or other stream, obtained from a para-xylene production process described herein. That is, such stream may provide a hydrocarbon component for an extractive distillation process as described herein. Still further advantages may be associated with negligible toxicity of extractive agent compounds described herein, or at least reduced toxicity relative to conventional agents.

Other embodiments of the invention are directed to liquid mixtures comprising ethylbenzene, a further $C_8$ aromatic compound, and an extractive agent compound as described herein, wherein the extractive agent compound is present in an amount effective to provide improved efficiency or separability, which may be quantified in terms of increasing relative volatility of ethylbenzene to the further $C_8$ aromatic compound, or may alternatively be quantified in terms of a competitive factor, D, as described herein, of greater than 1.

Yet other embodiments are directed to a continuous extractive distillation process comprising a number of integrated steps, including (a) recovering, as a bottoms fraction from an upstream distillation of an impure feed stream (e.g., an impure ethylbenzene-containing mixture as described herein, such as an impure ethylbenzene-containing feed to a xylene column), a purified feed steam comprising ethylbenzene and a further $C_8$ aromatic compound, wherein the purified feed stream is depleted in non-aromatic hydrocarbons (and optionally enriched in $C_8$ aromatic compounds), relative to the impure feed stream; (b) distilling a liquid mixture of the purified feed stream and an extractive agent compound to provide (i) an overhead fraction enriched in ethylbenzene (and optionally depleted in both the further $C_8$ aromatic compound and the extractive agent), relative to the liquid mixture, and (ii) a bottoms fraction that, relative to the liquid mixture, is enriched in both the further $C_8$ aromatic compound and the extractive agent compound (and optionally depleted in ethylbenzene); (c) distilling the bottoms fraction to provide (i) a second bottoms fraction enriched in the extractive agent compound (and optionally depleted in the further $C_8$ aromatic compound), relative to the bottoms fraction, and (ii) a second overhead fraction enriched in the further $C_8$ aromatic compound (and optionally depleted in the extractive agent compound), relative to the bottoms fraction; and (d) recycling at least a portion of the second bottoms fraction to provide at least a portion of the extractive agent compound in the liquid mixture in step (b).

The distilling of the liquid mixture in step (b) may be performed in one or more (e.g., a series) of distillation columns, to which some or all of the second bottoms fraction is recycled in step (d). Optionally, a fresh or make-up stream comprising the extractive agent compound may be added to provide at least a second portion of the extractive agent compound in the liquid mixture in step (b).

Still other embodiments of the present invention are directed to the use of one or more extractive agent compound(s) as described herein, in an extractive distillation process for separating ethylbenzene from a hydrocarbon component as described herein. In any of the aforementioned embodiments, a fraction enriched in ethylbenzene may be recovered as an ethylbenzene rich product.

These and other aspects, embodiments, and associated advantages will become apparent from the following Detailed Description.

BRIEF DESCRIPTION OF THE DRAWINGS

The flow schemes of FIGS. 1 and 2 are to be understood to present an illustration of the invention and/or principles involved. Details including pumps, compressors, heaters, chillers, reboilers, condensers, liquid and vapor reflux loops, instrumentation and control loops, and other items not essential to the understanding of the invention are not shown. As is readily apparent to one of skill in the art having knowledge of the present disclosure, extractive distillation methods, according to various other embodiments of the invention, will have configurations and components determined, in part, by their specific use.

DETAILED DESCRIPTION OF EMBODIMENTS

General Terms

The term "extractive agent compound" refers to a compound that interacts with two other compounds to facilitate their separation by distillation. These interactions, in the environment of a liquid mixture comprising the extractive agent compound and such two other compounds (e.g. ethylbenzene and a further $C_8$ aromatic hydrocarbon) may effectively decrease the boiling point of the one other compound having the lower normal boiling point (e.g., ethylbenzene) and/or effectively increase the boiling point of the second other compound having the higher normal boiling point (e.g., para-xylene). Therefore, in the environment of the liquid mixture, the difference in the effective boiling points of two closely-boiling compounds may be increased, compared to the difference in the normal boiling points of these compounds. According to representative embodiments, two compounds to be separated using extractive distillation processes described herein (e.g., one other compound, enriched in an overhead fraction, and a second other compound, enriched in a bottoms fraction) have normal boiling points that generally differ by generally less than about 15° C. (27° F.), typically by less than about 10° C. (18° F.), and often by less than about 5° C. (9° F.), such that these compounds are not easily separable using conventional distillation (i.e., in the absence of an extractive agent compound), without significant capital expenditures (associated with a large number of vapor-liquid equilibrium separation stages within a column) and/or significant energy expenditure (associated with high liquid and vapor reflux flows and high reboiler and condenser duties).

The term "extractive distillation process" refers to a distillation process using an extractive agent compound (e.g., present in a liquid mixture that is subjected to heating and multiple stages of vapor-liquid equilibrium separation). In representative embodiments, two or more extractive agent compounds as described herein may be used.

In other representative embodiments, one or more extractive agent compounds as described herein may be used, in combination with one or more conventional extractive agent compounds, and/or one or more further constituents (e.g., one or more solvents) of an overall extractive agent solution. One or more extractive agent compounds as described herein may be present in such extractive agent solution, in a combined amount of such extractive agent compounds of generally at least about 10 wt-%, typically at least about 60 wt-%, and often at least about 80 wt-%, with the balance comprising, for example, one or more conventional extractive agent compounds and/or one or more solvents. According to any embodiment described herein, therefore, the term "extractive agent compound" may be replaced with "extractive agent solution," wherein the latter indicates the possibility of constituents other than extractive agent compound (s) according to the present invention.

The term "mixture" refers to any combination of more than one compound. A representative liquid mixture, which is used in an extractive distillation process, comprises one or more extractive agent compound(s) according to the present invention, in combination with a hydrocarbon component comprising at least two different hydrocarbon compounds, such as ethylbenzene and a further $C_8$ aromatic compound that is other than ethylbenzene.

The term "cyclic ring structure" denotes a structure of, or included in, a compound or molecule, which structure includes three or more atoms (e.g., from three to ten atoms, from five to eight atoms, or from six to seven atoms) arranged or bonded in a ring. The term "cyclic ring structure" encompasses both "carbocyclic ring structure," in the case of the ring being formed solely by carbon atoms, and "heterocyclic ring structure," in the case of the ring being formed by carbon atoms and at least one atom that is not carbon (e.g., oxygen, nitrogen, or sulfur). An aromatic compound, as is understood in the art, is a compound or molecule comprising an aromatic ring structure, which is known as a planar (flat) structure, formed by carbon atoms, and optionally heteroatoms, in a ring of resonance bonds that exhibits more stability, compared to other geometric or connective arrangements with the same number of carbon atoms. If all ring members of an aromatic ring structure are carbon atoms, then this ring structure is both "carbocyclic" and "aromatic" (i.e., some "aromatic" ring structures can fall within "carbocyclic" ring structures). Aromatic compounds are preferably benzene derivatives, i.e., compounds comprising a benzene ring that is substituted at one or more carbon atoms forming the ring. The term "$C_8$ aromatic compound" refers to an aromatic compound with eight carbon atoms.

Hydrocarbon Components and Liquid Mixtures

Extractive distillation processes can comprise distilling a mixture comprising a hydrocarbon component and, advantageously, an extractive agent compound as described herein. The hydrocarbon component may comprise both aromatic and non-aromatic hydrocarbons, and in representative embodiments it comprises aromatic hydrocarbons in a combined amount of generally at least about 50% by weight (wt-%), typically at least about 85% wt-%, and often at least about 95% wt-%. In each case, the balance may be all or substantially all non-aromatic (e.g., paraffinic, cycloparaffinic, and/or naphthenic) hydrocarbons. For example, the hydrocarbon component may comprise non-aromatic hydrocarbons in a combined amount of generally less than about 50% wt-%, typically less than about 15% wt-%, and often less than about 5% wt-%. These weight percentages as described with respect to combined amounts of aromatic hydrocarbons, or combined amounts of non-aromatic hydrocarbons, present in the hydrocarbon component, may be weight percentages generally of $C_5$-$C_9$ aromatic hydrocarbons or $C_5$-$C_9$ non-aromatic hydrocarbons present, but more typically are weight percentages of $C_6$-$C_8$ aromatic hydrocarbons or $C_6$-$C_8$ non-aromatic hydrocarbons present, and often weight percentages of $C_8$ aromatic hydrocarbons or $C_8$ non-aromatic hydrocarbons present.

According to some embodiments, the hydrocarbon component may be obtained as a purified feed stream, following one or more upstream distillations of an impure feed, to remove non-aromatic hydrocarbons and/or other species that could impact the efficiency with which the extractive distillation is performed. Particular types of non-aromatic hydrocarbons that may be removed include $C_8$ paraffinic hydrocarbons (e.g., n-octane and isomers of iso-octane), $C_7$-$C_8$ cycloparaffinic hydrocarbons (e.g., ethylcyclohexane and cyclooctane), $C_9$ naphthenic hydrocarbons (e.g., isomers of trimethylcyclohexane) and others. For example, upstream distillation of an impure feed stream may be performed to provide a hydrocarbon component comprising ethylbenzene and a further $C_8$ aromatic compound, depleted in non-aromatic hydrocarbons, relative to the impure feed stream. In this case, the hydrocarbon component may be recovered as a bottoms fraction from this upstream distillation. Alternatively, two upstream distillations (e.g., a first and a second upstream distillation) may be performed to recover first an intermediate purity hydrocarbon component, depleted in heavy hydrocarbons (e.g., $C_9$+ hydrocarbons), relative to the impure feed (e.g., a heavy hydrocarbon-contaminated feed), and to recover second the hydrocarbon component, depleted in non-aromatic hydrocarbons, relative to the intermediate purity hydrocarbon component. In this case, the intermediate purity hydrocarbon component may be recovered as an overhead fraction from the first upstream distillation, and the hydrocarbon product may be recovered as a bottoms fraction from the second upstream distillation. According to other embodiments, the order with which various fractions are recovered and/or removed in two or more upstream distillations may be varied, depending on the types and amounts of species to be removed, to improve overall operating efficiency in obtaining the hydrocarbon component.

The hydrocarbon components of liquid mixtures for use in extractive distillation processes described herein, may generally be obtained from a refinery operation, such as naphtha reforming to produce gasoline boiling-range hydrocarbons. The hydrocarbon components may also be obtained from naphtha cracking. Representative hydrocarbon components, such as ethylbenzene-containing hydrocarbon components, include "high ethylbenzene" streams, for example, streams generally containing at least 50% wt-%, typically at least 60 wt-%, and often at least 75 wt-%, of ethylbenzene, such as streams obtained from naphtha cracker processes, with exemplary streams being recovered from pyrolysis gasoline that is generated in these processes, as described above. Other ethylbenzene-containing hydrocarbon components include "low ethylbenzene" streams, for example, streams generally containing less than 40% wt-%, typically less than 20% wt-%, and often less than 10 wt-%) of ethylbenzene, such as streams obtained from the production of para-xylene, in which a mixed $C_8$ hydrocarbon stream is separated from a reformate stream that is a feed to a xylene column.

The ethylbenzene-containing hydrocarbon component may generally comprise $C_8$ aromatic compounds in a combined amount of at least about 70 wt-% (e.g., as the combined amount of ethylbenzene and the xylene isomers, ortho-xylene, meta-xylene, and para-xylene), of this component, and will typically comprise $C_8$ aromatic compounds in a combined amount of at least about 85 wt-%, and often at least about 95 wt-%. Representative ethylbenzene-containing hydrocarbon components comprise one or more further $C_8$ aromatic hydrocarbons, other than ethylbenzene, with these further $C_8$ aromatic hydrocarbons being present in the hydrocarbon component in any amount, for example in an amount from about 10 wt-% to about 90 wt-%, from about 15 wt-% to about 80 wt-%, or from about 35 wt-% to about 75 wt-%. With respect to the further $C_8$ aromatic hydrocarbon portion only, this portion may comprise all or substantially all (e.g., greater than 95 wt-%) of (i) ortho-xylene, meta-xylene, and para-xylene in combination, (ii) meta-xylene and para-xylene in combination, or (iii) para-xylene.

Liquid mixtures, which are subjected to extractive distillation, may be formed by combining a hydrocarbon component, such as an ethylbenzene-containing hydrocarbon component, with one or more extractive agent compounds. In exemplary processes described herein, this combining may be performed batchwise, but it is preferably performed continuously. This combining may be performed prior to the extractive distillation, such as in the case of continuously combining streams of the hydrocarbon component and the extractive agent compound(s) upstream of a distillation column used to perform the extractive distillation. This combining may alternatively be performed within the extractive distillation itself, such as in the case of continuously feeding the hydrocarbon component and the extractive agent compound(s), as separate feed streams to a distillation column used to perform the extractive distillation. For example, these separate feed streams may be introduced to the distillation column at the same axial (vertical) height or different heights.

Representative liquid mixtures comprise a hydrocarbon component and one or more extractive agent compound(s) as described above. Representative weight ratios of the hydrocarbon component to the extractive agent compounds may range generally from about 1:10 to about 50:1, typically from about 1:8 to about 20:1, and often from about 1:6 to about 1:1. The liquid mixture may comprise all or substantially all hydrocarbon component and extractive agent compound(s), with no or substantially no additives. In representative embodiments, the liquid mixture may comprise the hydrocarbon component and extractive agent compound(s) generally in a combined amount of at least about 70 wt-%, typically at least about 85% wt-%, and often at least about 95 wt-%, of the liquid mixture. According to other embodiments, water may be included in the liquid mixture, for example in an amount generally from about 0.005 wt-% to about 25 wt-%.

In some cases, a low water content of the liquid mixture may be desirable. For example, the liquid mixture may have a water content of generally less than about 3 wt-%, typically less than about 1 wt-%, and often less than about 0.1 wt-% or even less than about 0.01 wt-%. If a low water content is desired, this may be achieved by drying (dehydrating) the hydrocarbon component, the extractive agent compound(s), or both (e.g., drying both of these in combination or drying each of these separately). Drying may be performed using, for example, distillation, aqueous-organic phase extraction, adsorption, or other techniques and even combinations of such techniques, generally prior to distilling the liquid mixture. According to a specific example, the hydrocarbon component may be dried by contact with a suitable molecular sieve (e.g., an aluminosilicate molecular sieve such as type 3A available from Sigma-Aldrich). The representative water contents described above with respect to the liquid mixture are also applicable to the hydrocarbon component and/or the extractive agent compound(s) individually.

More generally, the liquid mixture may be characterized, in some embodiments, as having only limited amounts of low-boiling and/or high-boiling impurities, whereby a low-boiling impurity may generally have boiling point of less than about 130° C. (266° F.) and a high boiling point may generally have a boiling point of greater than about 150° C. (302° F.). For example, the liquid mixture may include a low-boiling fraction (i.e., total contribution of all species having a normal boiling point of less than about 130° C. or 266° F.) and/or a high-boiling fraction (i.e., total contribution of all species having a normal boiling point of greater than about 150° C. or 302° F.) representing less generally less than about 10 wt-%, typically less than about 5 wt-%, and often less than about 2 wt-%, based on total weight of the liquid mixture. The boiling range of species present in the liquid mixture may be suitably narrowed by fractionation to remove low-boiling impurities (e.g., non-aromatic compounds and/or water) and/or high-boiling impurities (e.g., $C_9^+$ hydrocarbons), prior to distilling the liquid mixture, for example as discussed in greater detail below.

Extractive Agent Compounds

For extractive agent compounds used in the processes described herein, the binding energy between such an extractive agent compound and ethylbenzene advantageously differs from the binding energy between the extractive agent compound and the further (e.g., non-ethylbenzene) $C_8$ aromatic compound, such as para-xylene. Binding energy is determined by a combination of several factors associated with the respective interacting compounds, including their polarity and steric effects. It now has been surprisingly discovered that extractive agent compounds having a carbocyclic (e.g., and also aromatic) or heterocyclic ring structure being substituted at substitutable ring positions with (i) at least one $NR^aR^b$ radical (i.e., —$NR^aR^b$ substituent), wherein $R^a$ and $R^b$ are independently selected from the group consisting of an oxygen radical, a hydrogen radical, and a hydrocarbyl radical having from about 1 to about 20 carbon atoms, and (ii) at least two halo radicals (i.e., halo substituents derived from their respective halogen atoms) are effective extractive agents for extractive distillation, such as for use in the separation of ethylbenzene from one or more further $C_8$ aromatic compounds, preferably xylenes (e.g., one or both of meta-xylene and para-xylene). While not being bound by theory, it is believed that the presence of both nitrogen and halogen atoms, together with the cyclic (e.g. aromatic) ring structure provide appropriate polarity, whereas the cyclic (e.g., aromatic) base structure itself provides important steric effects. As a result, extractive agent compounds comprising these features in combination can attractively interact with non-ethylbenzene $C_8$ aromatic compounds, but can repulsively interact with ethylbenzene, thereby facilitating the distillative separation of non-ethylbenzene $C_8$ aromatic compounds and the extractive agent compound(s) in a bottoms fraction and ethylbenzene in an overhead fraction.

According to representative embodiments, the extractive agent compound is a compound according to Formula (I):

(I)

wherein $R^a$ and $R^b$ are each bonded to the nitrogen atom illustrated in this formula and are independently selected from the group consisting of an oxygen radical, a hydrogen radical, and a hydrocarbyl radical having from about 1 to about 20 carbon atoms. $R^a$ and $R^b$ are each bonded to the nitrogen atom shown in Formula (I) above via a single covalent bond, a double covalent bond, or a resonance stabilized covalent bond.

In the case of both $R^a$ and $R^b$ being an oxygen radical, the radical group —$NR^aR^b$ represents nitro (—$NO_2$), as a substituent of the benzene ring illustrated Formula (I), with nitro having a structure that can be represented as or alternatively represented with resonance stabilization as In the case of both $R^a$ and $R^b$ being hydrogen, the radical group —$NR^aR^b$ represents a primary amino group (—$NH_2$).

Otherwise, $R^a$ and $R^b$, together with the nitrogen atom shown in Formula (I) above to which they are commonly bonded, may form a 5- to 8-membered ring, wherein one or more ring members (e.g., carbon atom ring members) may be substituted. Suitable substituents of the ring members are those substituents identified below as substituents (1) or (2) of one or more carbon atoms of a hydrocarbyl radical. According to exemplary embodiments, $NR^aR^b$ may form a 5-membered ring substituent, such as pyrrolyl, dihydropyrrolyl, tetrahydropyrrolyl, or pyrrolidinyl, or alternatively may form a 6-membered ring substituent, such as pyridinyl, dihydropyridinyl, tetrahydropyridinyl, or piperidinyl.

In formula (I) above, $R^2$-$R^6$ are substituents of the benzene ring illustrated in this formula (other than the substituent, $NR^aR^b$) and are independently selected from the group consisting of halo, a hydrogen radical, and a hydrocarbyl radical having from about 1 to about 20 carbon atoms. Preferably, at least two of $R^2$-$R^6$ are halo, as in the case of such at least two of $R^2$-$R^6$ being chloro. For example, $R^3$ and $R^4$ may both be halo, such as chloro. Alternatively, $R^2$ and $R^3$ may both be halo, such as chloro.

In the case of one or more of $R^a$, $R^b$, $R^2$, $R^3$, $R^4$, $R^5$, or $R^6$ being a hydrocarbyl radical having from about 1 to about 20 carbon atoms, such a hydrocarbyl radical refers namely to a saturated or partially unsaturated straight chain, branched, or cyclic radical of a hydrocarbon, in which one or more carbon atoms in such hydrocarbyl radical are optionally substituted and/or replaced, for example substituted according to (1) and/or (2) below, or replaced according to (3) below. In particular, in representative hydrocarbyl radicals having from about 1 to about 20 carbon atoms, (1) one or more carbon atoms having one or more bound hydrogen atoms (i.e., hydrogen radicals) are optionally substituted with a monovalent radical independently selected from alkyl, alkenyl, alkynyl, cycloalkyl, heterocycloalkyl, aryl, heteroaryl, —OH, —SH, —SOH, —$SO_2H$, —$SO_3H$, —$NH_2$, —$NO_2$, —$CO_2H$, —$CONH_2$, —CN, —F, —Cl, —Br, and —I, wherein the monovalent heteroatomic radicals —OH, —SH, —SOH, —$SO_2H$, —$SO_3H$, —$NH_2$, —CO$_2$H, —CONH$_2$ optionally have one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;

(2) one or more carbon atoms having two or more bound hydrogen atoms are optionally substituted with a divalent radical independently selected from =O, =S, =NH, =NOH, and =NNH$_2$, wherein the divalent heteroatomic radicals =NH, =NOH, and =NNH$_2$ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and (3) one or more methylene carbon atoms (—CH$_2$—) are optionally replaced by a divalent radical independently selected from alkyl, alkenyl, alkynyl, cycloalkyl, heterocycloalkyl, aryl, heteroaryl, —O—, —S—, —NH—, —OCO—, —CO$_2$—, —CONH—, —OCONH—, and —CO$_2$NH—, wherein the divalent heteroatomic radicals —NH—, —CONH—, —OCONH—, and —CO$_2$NH— optionally have one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

According to other embodiments, one or both of $R^a$ and $R^b$, and/or one or more of $R^2$, $R^3$, $R^4$, $R^5$, or $R^6$ (e.g., those substituents $R^2$, $R^3$, $R^4$, $R^5$, or $R^6$ that are not halo) may otherwise be independently selected from, in addition to a hydrogen radical or hydrocarbyl radical having from about 1 to about 20 carbon atoms as defined above, a monovalent heteroatomic radical such as —OH, —SH, —SOH, —SO$_2$H, —SO$_3$H, —NH$_2$, —NO$_2$, —CO$_2$H, —CONH$_2$, and —CN, wherein the monovalent heteroatomic radicals —OH, —SH, —SOH, —SO$_2$H, —SO$_3$H, —NH$_2$, —CO$_2$H, and —CONH$_2$ optionally have one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

A representative hydrocarbyl radical having from about 1 to about 20 carbon atoms may be a saturated or partially unsaturated straight chain, branched, or cyclic radical of a hydrocarbon, optionally in which no carbon atom is substituted according to (1) above, or in which no carbon atom is substituted according to (2) above, or in which no carbon atom is replaced according to (3) above. In the case of a saturated cyclic radical of a hydrocarbon, a representative hydrocarbyl radical may be cycloalkyl (e.g., cyclopentyl or cyclohexyl). In the case of a partially unsaturated cyclic radical of a hydrocarbon, a representative hydrocarbyl radical may be aryl (e.g., cyclopentadienyl or phenyl).

A representative hydrocarbyl radical having from about 1 to about 20 carbon atoms may be a saturated straight chain, branched, or cyclic radical of an aliphatic hydrocarbon, optionally in which no carbon atom is substituted according to (1) above, or in which no carbon atom is substituted according to (2) above, or in which no carbon atom is replaced according to (3) above.

A representative hydrocarbyl radical having from about 1 to about 20 carbon atoms may be selected from the group consisting of alkyl, alkenyl, alkynyl, cycloalkyl, heterocycloalkyl, aryl, heteroaryl, (cycloalkyl)alkyl, (heterocycloalkyl)alkyl, aralkyl, heteroaralkyl, hydroxy, alkoxy, cycloalkoxy, aryloxy, hydroxycarbonyl, hydroxycarbonylalkyl, alkanoyl, alkanoyloxy, alkoxycarbonyl, thiol, alkylthiol, amino, halo, haloalkyl, amido, alkylamido, (cycloalkyl)amido, (heterocycloalkyl)amido, arylamido, and (heteroaryl)amido.

A representative hydrocarbyl radical having from about 1 to about 20 carbon atoms may be alkyl, such as $C_1$-$C_4$ alkyl (e.g., methyl, ethyl, propyl, and butyl).

According to other embodiments, one or both of $R^a$ and $R^b$, and/or one or more of $R^2$, $R^3$, $R^4$, $R^5$, or $R^6$ (e.g., those substituents $R^2$, $R^3$, $R^4$, $R^5$, or $R^6$ that are not halo), for example both of $R^a$ and $R^b$, and/or all of $R^2$, $R^3$, $R^4$, $R^5$, or $R^6$ that are not halo, are hydrogen radicals.

According to some embodiments, in which both $R^a$ and $R^b$ in the extractive agent compound according to Formula (I) are an oxygen radical and the radical group —NR$^a$R$^b$ represents nitro (—NO$_2$), the extractive agent compound may be a halo-substituted nitrobenzene, according to which one or more of (e.g., at least two of) $R^2$-$R^6$ may be halo. For example, both $R^2$ and $R^3$, or both $R^3$ and $R^4$, may be halo, and optionally the remaining substituents may be hydrogen. According to specific embodiments, the aromatic compound of the extractive agent may be an isomer of dichloronitrobenzene, for example a compound in which NR$^a$R$^b$ represents nitro (—NO$_2$), two of the substituents $R^2$, $R^3$, $R^4$, $R^5$, and $R^6$ represent chloro, and the remaining substituents $R^2$, $R^3$, $R^4$, $R^5$, and $R^6$ represent hydrogen. In the particular case in which NR$^a$R$^b$ represents nitro (NO$_2$); $R^3$ and $R^4$ represent chloro; and $R^2$, $R^5$, and $R^6$ represent hydrogen, the aromatic compound of the extractive agent is 1,2-dichloro-4-nitrobenzene. In the particular case in which NR$^a$R$^b$ represents nitro (NO$_2$); $R^2$ and $R^3$ represent chloro; and $R^3$, $R^5$, and $R^6$ represent hydrogen, the aromatic compound of the extractive agent is 1,2-dichloro-3-nitrobenzene. The compounds 1,2-dichloro-4-nitrobenzene and 1,2-dichloro-3-nitrobenzene have the following structures:

1,2-dichloro-3-nitrobenzene and 1,2-dichloro-4-nitrobenzene

According to other embodiments, in which both $R^a$ and $R^b$ in the extractive agent compound according to Formula (I) are a hydrogen radical and the radical group —NR$^a$R$^b$ represents amino (—NH$_2$), the extractive agent compound may be a halo-substituted aminobenzene, according to which one or more of (e.g., at least two of) $R^2$-$R^6$ may be halo. For example, both $R^2$ and $R^3$, or both $R^3$ and $R^4$, may be halo, and optionally the remaining substituents may be hydrogen. According to specific embodiments, the aromatic compound of the extractive agent may be an isomer of dichloroaniline, for example a compound in which NR$^a$R$^b$ represents amino (—NH$_2$), two of the substituents $R^2$, $R^3$, $R^4$, $R^5$, and $R^6$ represent chloro, and the remaining substituents $R^2$, $R^3$, $R^4$, $R^5$, and $R^6$ represent hydrogen. In the particular case in which NR$^a$R$^b$ represents amino (NH$_2$); $R^3$ and $R^4$ represent chloro; and $R^2$, $R^5$, and $R^6$ represent hydrogen, the aromatic compound of the extractive agent is 3,4-dichloroaniline. This compound has the following structure:

3,4 dichloroaniline

Mixtures of any two or more extractive agent compounds, such as two or more compounds according to Formula (I) above, may also be used, for example in a liquid mixture (LM) of an extractive distillation process described above. According to particular embodiments, a mixture of an isomer of dichloroaniline and an isomer of dichloronitrobenzene, such as a mixture of (i) 3,4-dichloroaniline and (ii) 1,2-dichloro-4-nitrobenzene or 1,2-dichloro-3-nitrobenzene, at any mixing ratio (e.g., 5/95 w/w of (i):(ii), 25/75 w/w of (i):(ii), 50/50 w/w of (i):(ii), 75/25 w/w of (i):(ii), or 95/5 of (i):(ii)) may be used.

For purposes of the present invention, and consistent with accepted chemical nomenclature for radicals such as substituent groups, "Halo," alone or in combination, represents a halogen radical selected from fluoro, chloro, bromo, and iodo (i.e., —F, —Cl, —Br, and —I, respectively). According to preferred embodiments, "halo" represents fluoro or chloro, and more preferably represents chloro.

"Alkyl," as used alone or in combination with other radicals (i.e., alone or in combination), represents a straight or branched chain saturated hydrocarbon radical, which may be bonded at one end of the chain (e.g., as in a methyl group, —CH$_3$) or at two ends of the chain (e.g., as in a methylene group —CH$_2$—). Unless otherwise indicated, alkyl contains from 1 to 10 carbon atoms. "Alkenyl," alone or in combination, represents alkyl that contains one or more carbon-to-carbon double bonds. "Alkynyl," alone or in combination, represents alkyl that contains one or more carbon-to-carbon triple bonds.

"Cycloalkyl," alone or in combination, represents a monocyclic, bridged monocyclic, bicyclic, tricyclic or spiro ring saturated hydrocarbon radical, which may be bonded to a parent molecule at one or more (e.g., one or two) bonding sites, wherein each ring contains from 3 to 8 carbon atoms. "Heterocycloalkyl," alone or in combination, represents cycloalkyl having one or more carbon atoms replaced by an oxygen, nitrogen, or sulfur (including sulfoxide and sulfone), or otherwise replaced by a divalent radical having such heteroatom, such as =NH, =NOH, =NNH$_2$, =SO and =SO$_2$. "Aryl," alone or in combination, represents an unsaturated or partially unsaturated monocyclic, bridged monocyclic, bicyclic, tricyclic or spiro ring hydrocarbon radical, which may be bonded to a parent molecule at one or more (e.g., one or two) bonding sites, wherein each ring contains from 3 to 8 carbon atoms. "Heteroaryl," alone or in combination, represents aryl having one or more carbon atoms replaced by an oxygen, nitrogen, or sulfur heteroatom, or otherwise replaced by a divalent radical having such heteroatom, such as =NH, =NOH, =NNH$_2$, =SO, and =SO$_2$. Unless otherwise indicated or apparent from the name of a specific cycloalkyl, heterocycloalkyl, aryl, or heteroaryl radical, these cyclic radicals may be bonded in the molecules described herein at any ring positions available for bonding (i.e., at any substitutable ring position).

"Aralkyl," alone or in combination, represents alkyl in which a hydrogen atom is replaced by aryl. "Aralkenyl," alone or in combination, represents alkenyl in which a hydrogen atom is replaced by aryl. "Aralkynyl," alone or in combination, represents alkynyl in which a hydrogen atom is replaced by aryl. "Heteroaralkyl," "heteroaralkenyl," and "heteroaralkynyl," alone or in combination, represent alkyl, alkenyl, and alkynyl, respectively, in which a hydrogen atom is replaced by heteroaryl.

"Hydroxy," alone or in combination, represents the radical —OH. "Alkoxy," "alkenoxy," and "alkynyloxy," alone or in combination, represent alkyl, alkenyl, and alkynyl, respectively, that are bonded to a molecule through an —O— linkage. For example, alkoxy, alone or in combination, represents the radical alkyl-O—. "Cycloalkoxy," "heterocycloalkoxy," "aryloxy," and "heteroaryloxy," alone or in combination, represent cycloalkyl, heterocycloalkyl, aryl, and heteroaryl, respectively, that are bonded to a molecule through an —O— linkage.

"Carbonyl," alone or in combination, represents the radical —(C=O)—. "Thiocarbonyl," alone or in combination, represents the radical —(C=S)—. "Hydroxycarbonyl," alone or in combination, represents a radical of formic acid, —(C=O)—OH. "Alkanoyl," "alkenoyl," "alkynoyl," alone or in combination, represent alkyl, alkenyl, and alkynyl, respectively, that are bonded to a molecule through a carbonyl linkage. For example, alkanoyl, alone or in combination, represents the radical alkyl-(C=O)—. "Cycloalkanoyl," "heterocycloalkanoyl," "aroyl," and "heteroaroyl," alone or in combination, represent cycloalkyl, heterocycloalkyl, aryl, and heteroaryl, respectively, that are bonded to a molecule through a carbonyl linkage.

"Carbonyloxy," alone or in combination, represent carbonyl that is bonded to a molecule through an —O— linkage. "Alkanoyloxy," "alkenoyloxy," "alkynoyloxy," "cycloalkanoyloxy," "heterocycloalkanoyloxy," "aroyloxy," and "heteroaroyloxy," alone or in combination, represent alkanoyl, alkenoyl, alkynoyl, cycloalkanoyl, heterocycloalkanoyl, aroyl, and heteroaroyl, respectively, that are bonded to a molecule through an —O— linkage. For example, alkanoyloxy represents the radical alkyl-C(=O)—O—.

"Thiol," alone or in combination, represents an —S— or —SH linkage. "Alkylthiol," "alkenylthiol," and "alkynylthiol," alone or in combination, represent alkyl, alkenyl, and alkynyl, respectively, that are bonded to a molecule through an —S— linkage. For example, alkylthiol represents the radical alkyl-S—. "Thiolalkyl," "thiolalkenyl," and "thiolalkynyl," alone or in combination, represent radicals of the formula HS-alkyl-, HS-alkenyl-, and HS-alkynyl-, respectively.

"Amino," alone or in combination, embraces radicals of both primary (—NH$_2$) and secondary (—NH—) amines. Unless otherwise indicated, both primary amino and secondary amino radicals may be substituted at a hydrogen, or at both hydrogens in the case of primary amino, with one or two radicals independently selected from the group consisting of alkyl, alkenyl, alkynyl, cycloalkyl, aryl, and heteroaryl. "Alkylamino," "alkenylamino," and "alkynylamino," alone or in combination, represent alkyl, alkenyl, and alkynyl, respectively, that are bonded to a molecule through a secondary amino (—NH—) linkage. "Amido," alone or in combination, represent a carbonylamino radical —(C=O)—NH—. "Alkylamido," "alkenylamido," and "alkynylamido," alone or in combination, represent alkyl, alkenyl, and alkynyl, respectively, that are bonded to a molecule through an amido linkage. For example, alkylamido refers to the radical alkyl-(C=O)—NH—. "Imino," alone or in combination, represents the radical —(C=NH)—, wherein, unless otherwise indicated, imino may be substituted at a hydrogen with a radical as defined above with respect to amino.

"Heteroatom(s)," "heteroatomic group(s)," and "heteroatomic radical(s)" represent atoms of oxygen, nitrogen, and sulfur, as well as groups and radicals having these heteroatoms, such as =O, =S, =NH, =NOH, and =NNH$_2$.

Representative Extractive Distillation Processes

Representative extractive distillation processes comprise distilling a liquid mixture comprising a hydrocarbon component and an extractive agent compound as described herein. A representative hydrocarbon component comprises ethylbenzene and at least one further C$_8$ aromatic compound. Accordingly, particular processes comprise distilling a liquid mixture comprising ethylbenzene, a further C$_8$ aromatic compound, and an extractive agent compound.

The performance of the extractive agent may be characterized according to its ability to increase relative volatility between ethylbenzene and the further C$_8$ aromatic compound to be separated, thereby increasing separation efficiency at each stage of vapor-liquid equilibrium. According to representative embodiments, the extractive agent compound may be present in the liquid mixture in an amount such that the relative volatility ($\alpha$) of ethylbenzene to the further C$_8$ aromatic compound is at least about 1.14, preferably at least about 1.16, more preferably at least about 1.20, and even more preferably at least about 1.22 at a given pressure, such as 200 millibar absolute pressure.

The performance of the extractive agent in extractive distillation processes described herein may alternatively be characterized by its competitive factor, with respect to ethylbenzene and the at least one further C$_8$ aromatic compound (e.g., meta-xylene or para-xylene) to be separated from ethylbenzene. The competitive factor (D) can be quantified by the expression $$D = \frac{\text{weight ratio ethylbenzene/further } C_8 \text{ aromatic compound (with extractive agent compound)}}{\text{weight ratio ethylbenzene/further } C_8 \text{ aromatic compound (without extractive agent compound)}}.$$

numerator of D is a vapor phase weight ratio of ethylbenzene to the further C$_8$ aromatic compound, at 80° C. (176° F.) and atmospheric pressure, in equilibrium with a liquid mixture of (i) 1 part by weight of 60 wt-% ethylbenzene and 40 wt-% of the further C$_8$ aromatic compound and (ii) 5 parts by weight of the extractive agent compound. The denominator of D is a reference a vapor phase weight ratio of the same compounds at 80° C. (176° F.) and atmospheric pressure, in equilibrium with the liquid composition of (i) only. Accordingly, values of D that exceed unity indicate an improvement in the ease of separability of ethylbenzene into the vapor phase, resulting from the presence of the extractive agent compound. This competitive factor may therefore be measured according to a standard protocol, for example as described herein. Advantageously, according to representative extractive distillation processes, the competitive factor may be generally at least about 1.10, typically at least about 1.18, and often at least about 1.20. Otherwise, an extractive agent may provide a competitive factor (D) that is less than unity, for example generally at most about 0.95, typically at most about 0.90, and often at most about 0.85, meaning that the extractive agent indicates an improvement in the ease of separability of the less volatile, further C$_8$ aromatic compound (e.g., meta-xylene or para-xylene) into the liquid phase.

Figure 1:
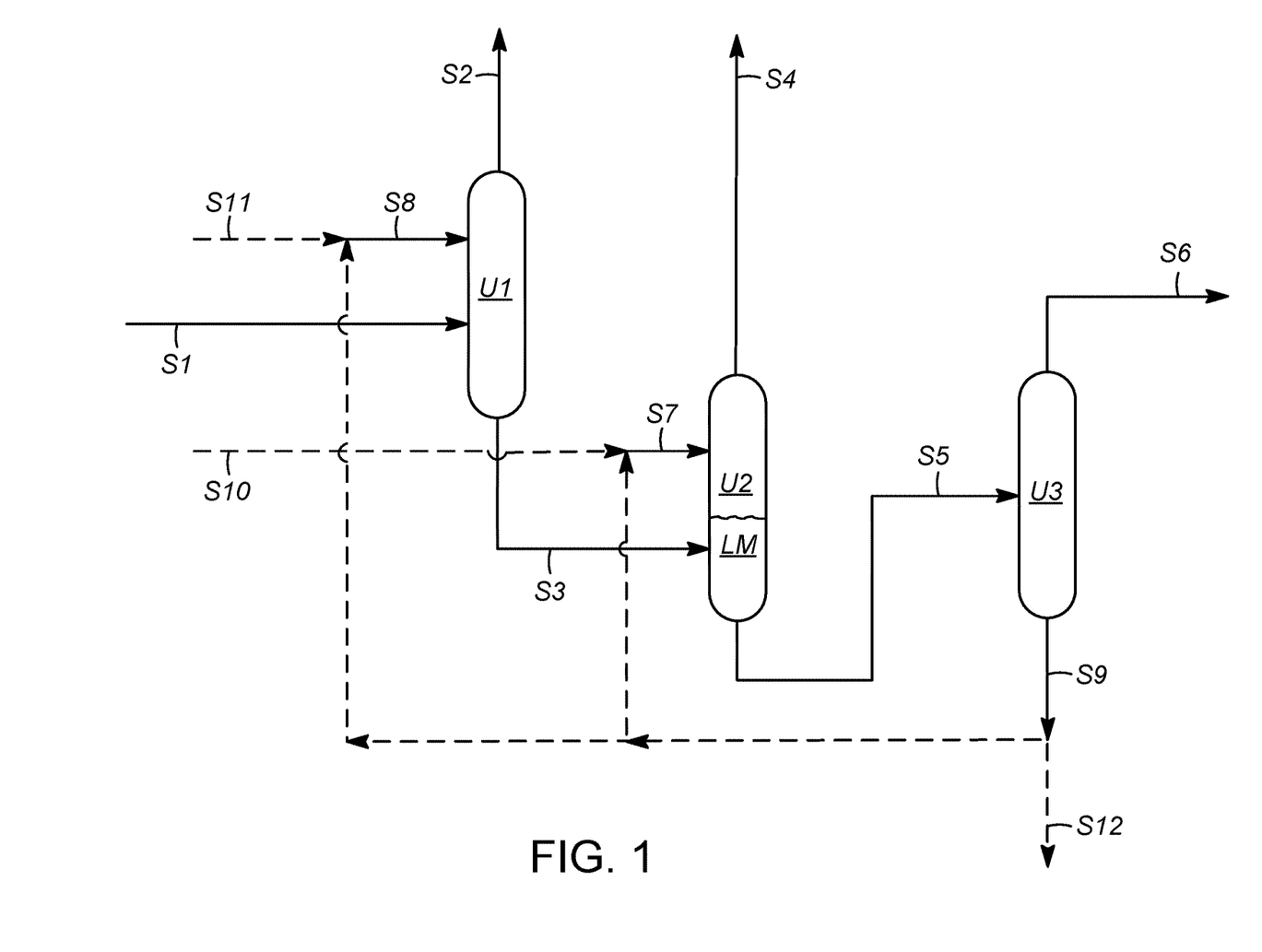
FIG. 1 illustrates a representative flow scheme according to one embodiment of an extractive distillation, including a pretreatment that is namely an upstream distillation to remove non-aromatic compounds from an impure feed stream, which non-aromatic compounds may have boiling points similar to ethylbenzene and/or the further $C_8$ aromatic compound present in the impure feed stream.

In some embodiments, alternative to, or in combination with, having a competitive factor, with respect to ethylbenzene and the other C$_8$ aromatic compound(s) as described above, a representative extractive agent compound or mixture of extractive agent compounds may have a competitive factor with respect to one or more non-aromatic hydrocarbons and ethylbenzene, which is greater than or less than unity. Advantageously, the extractive agent(s) can thereby facilitate the separation of such non-aromatic hydrocarbons from ethylbenzene and the other C$_8$ aromatic compound(s). For example, in the case of a competitive factor with respect to a given non-aromatic hydrocarbon that is greater than unity, the extractive agent can facilitate enriching the non-aromatic hydrocarbon in a low-boiling fraction or overhead removal fraction, as discussed in greater detail below in the case of non-aromatic removal column U1 (FIG. 1), upstream of extractive distillation column U2 (FIG. 1). The competitive factor D for a given non-aromatic hydrocarbon with respect to ethylbenzene may be determined in an analogous manner as described above but with the relevant weight ratios in the numerator and denominator being the weight ratio of a given non-aromatic compound to ethylbenzene, exceeding unity. According to particular embodiments, the extractive agent compound(s) may have a competitive factor D, (i) with respect to n-octane and ethylbenzene of generally at least about 2.0, typically at least about 2.3, and often at least about 2.6, (ii) with respect to ethylcyclohexane and ethylbenzene of generally at least about 1.7, typically at least about 1.9, and often at least about 2.1, and/or (iii) with respect to cyclooctane and ethylbenzene of generally at least about 1.6, typically at least about 1.7, and often at least about 1.8.

In representative embodiments, the desired relative volatility ($\alpha$), competitive factor (D), and/or other favorable extractive distillation operating characteristics are obtained upon distilling the liquid mixture at sub-atmospheric pressure, for example at an absolute pressure of generally less than about 800 millibar, typically less than about 400 millibar, and often less than about 300 millibar, with an exemplary pressure ranges being from about 50 millibar to about 800 millibar, from about 100 millibar to about 400 millibar, and from about 150 to about 300 millibar.

An exemplary flowscheme of an extractive distillation process is illustrated in FIG. 1. According to this embodiment, an impure feed stream (S1), for example comprising C$_8$ aromatic compounds (e.g., C$_8$ aromatic hydrocarbons such as both ethylbenzene and a further C$_8$ aromatic compound) but also one or more non-aromatic compounds (e.g., non-aromatic hydrocarbons such as n-octane and isomers of iso-octane, ethylcyclohexane, cyclooctane, and/or isomers of trimethylcyclohexane), is subjected to upstream distillation in non-aromatic removal column (U1). A non-aromatic extractive agent stream (S8) is combined with impure feed stream (S1), either prior to or within non-aromatic removal column (U1), to facilitate the desired removal of at least one of the non-aromatic compounds. As shown, an optional non-aromatic extractive agent compound make-up stream (S11) may also be introduced, continuously or intermittently, to non-aromatic removal column (U1), to replace any minor quantities of the non-aromatic extractive agent compound that are not recovered in recycle stream (S9). An overhead removal fraction (S2), enriched in the at least one non-aromatic compound and depleted in at least one $C_8$ aromatic compound, relative to the impure feed stream (S1), is withdrawn from non-aromatic removal column (U1), for example withdrawn as a non-aromatic compound enriched stream. This results in the removal of the at least one non-aromatic compound, which may have a boiling point comparable to, such as within 15° C. (+/−15° C. or +/−27° F.), within 10° C. (+/−10° C. or +/−18° F.), or possibly within 5° C. (+/−5° C. or +/−9° F.) of, a $C_8$ aromatic compound in impure feed stream (S1) (e.g., para-xylene, having a boiling point of 138° C. or 280° F.). As described above, particular types of non-aromatic hydrocarbons that may be removed include $C_8$ paraffinic hydrocarbons (e.g., n-octane and isomers of iso-octane), $C_7$-$C_8$ cycloparaffinic hydrocarbons (e.g., ethylcyclohexane and cyclooctane), $C_9$ naphthenic hydrocarbons (e.g., isomers of trimethylcyclohexane) and others. Non-aromatic removal column (U1) may also serve to remove water from impure feed stream (S1), for example to achieve a water content in pretreated bottoms fraction (S3) and/or liquid mixture (LM) as described above. Alternatively, impure feed stream (S1) may be subjected to a separate, optional water removal (WR) step, upstream of non-aromatic removal column, according to any of the methods described above. The removal of water may be economically advantageous, insofar as the total material being subjected to extractive distillation is reduced, and consequently the associated energy requirements. Other advantages may also result, in terms of separation performance.

Pretreated bottoms fraction (S3) is recovered from non-aromatic removal column (U1) (i.e., from this upstream distillation), as a purified feed stream to the extractive distillation. This purified feed stream is enriched, relative to the impure feed stream (S1), in both ethylbenzene and the further $C_8$ aromatic compound, as well as enriched in a non-aromatic extractive agent compound that is introduced to non-aromatic removal column (U1) with non-aromatic extractive agent stream (S8). Pretreated bottoms fraction (S3) is likewise depleted, relative to impure feed stream (S1) in one or more of the non-aromatic compounds present in this stream. Pretreated bottoms fraction (S3) is then introduced into extractive distillation column (U2) with a recycle portion (S7) of recycle stream (S9) comprising an ethylbenzene extractive agent, or namely an extractive agent compound as described herein. Pretreated bottoms fraction (S3) and recycle portion (S7) may be combined either prior to or within extractive distillation column (U2). Recycle portion (S7) therefore can provide some or all (at least a portion) of the extractive agent compound fed to extractive distillation column (U2). As shown, an optional extractive agent compound make-up stream (S10) may also be introduced, continuously or intermittently, to extractive distillation column (U2) to replace any minor quantities of the extractive agent compound that are not recovered in recycle stream (S9).

In extractive distillation column (U2), therefore, liquid mixture (LM) comprising pretreated bottoms fraction (S3) and the extractive agent compound present in recycle portion (S7) and optional make-up stream (S10) is distilled to provide overhead fraction (S4) that, relative to pretreated bottoms fraction (S3) and also relative to liquid mixture (LM), is enriched in ethylbenzene and depleted in both the extractive agent compound and at least one further $C_8$ aromatic compound (e.g., one or more isomers of xylene, such as meta-xylene and/or para-xylene) present in this pretreated bottoms fraction. Extractive distillation column (U2) also provides bottoms fraction (S5) that, relative to pretreated bottoms fraction (S3) and also relative to the liquid mixture, is enriched in both the at least one further $C_8$ aromatic compound and the extractive agent compound, and depleted in ethylbenzene. Therefore, according to some embodiments, extractive distillation column (U2) can advantageously serve to separate and recover overhead fraction (S4) as an ethylbenzene-rich product, which, depending on its purity, may have value for various industrial uses (e.g., styrene-monomer production). To purify and recover the extractive agent compound, bottoms fraction (S5) is then introduced to, and distilled in, extractive agent recovery column (U3) to provide second bottoms fraction (S9) that, relative to bottoms fraction (S5), is enriched in the extractive agent compound and optionally also enriched in the non-aromatic extractive agent compound. Second bottoms fraction (S9), relative to bottoms fraction (S5), is also depleted in the at least one further $C_8$ aromatic compound. In this manner, at least a portion of second bottoms fraction (S9) may then be recovered and recycled, as recycle portion (S7), to extractive distillation column (U2), to advantageously conserve material resources, by providing at least a portion of the extractive agent compound in liquid mixture (LM). Optionally, at least a second portion of second bottoms fraction (S9) may also be recycled, as non-aromatic extractive agent stream (S8), to non-aromatic removal column (U1). According to some embodiments, second bottoms fraction (S9), recycle portion (S7), and/or non-aromatic extractive agent stream (S8) may be further purified (e.g., using a further distillation, adsorbent separation, extraction etc.) to remove contaminants from these extractive agent-containing streams, prior to introduction to their respective columns. Optionally, second bottoms fraction bleed stream (S12) may be used to prevent an excessive accumulation of unwanted impurities in the recycle of extractive agents.

Distilling of bottoms fraction (S5) in extractive agent recovery column (U3) further provides second overhead fraction (S6) that, relative to bottoms fraction (S5), is enriched the at least one further $C_8$ aromatic compound and depleted in in the extractive agent compound and optionally also depleted in the non-aromatic extractive agent compound. The overall, integrated process thereby advantageously provides overhead fraction (S4) and second overhead fraction (S6) that are purified, respectively, in ethylbenzene and the one or more further $C_8$ aromatic compound(s) to advantageously resolve these purified products while also providing recycle of the extractive agent compound. One or both of these purified products may be further purified (e.g., using a further distillation, adsorbent separation, extraction etc.) to achieve a higher purity level if desired.

According to the particular embodiment illustrated in FIG. 1, the extractive agent compound used in the upstream non-aromatic removal column (U1), as well as in the extractive distillation column (U2) (and in each case separated from the second bottoms fraction (S9)) may be the same compound. Alternatively, different extractive agent compounds may be used for these different purposes, in which case an optional separation (e.g., distillation) may be used to obtain the non-aromatic extractive agent stream (S8) and the recycle portion (S7) that are introduced to these respective columns. An exemplary non-aromatic extractive agent is acetonitrile. Preferably, however, the same compound may be used for both extractive distillations, leading to further advantages in terms of process simplification (e.g., fewer separation requirements) and associated cost reductions.

Figure 2:
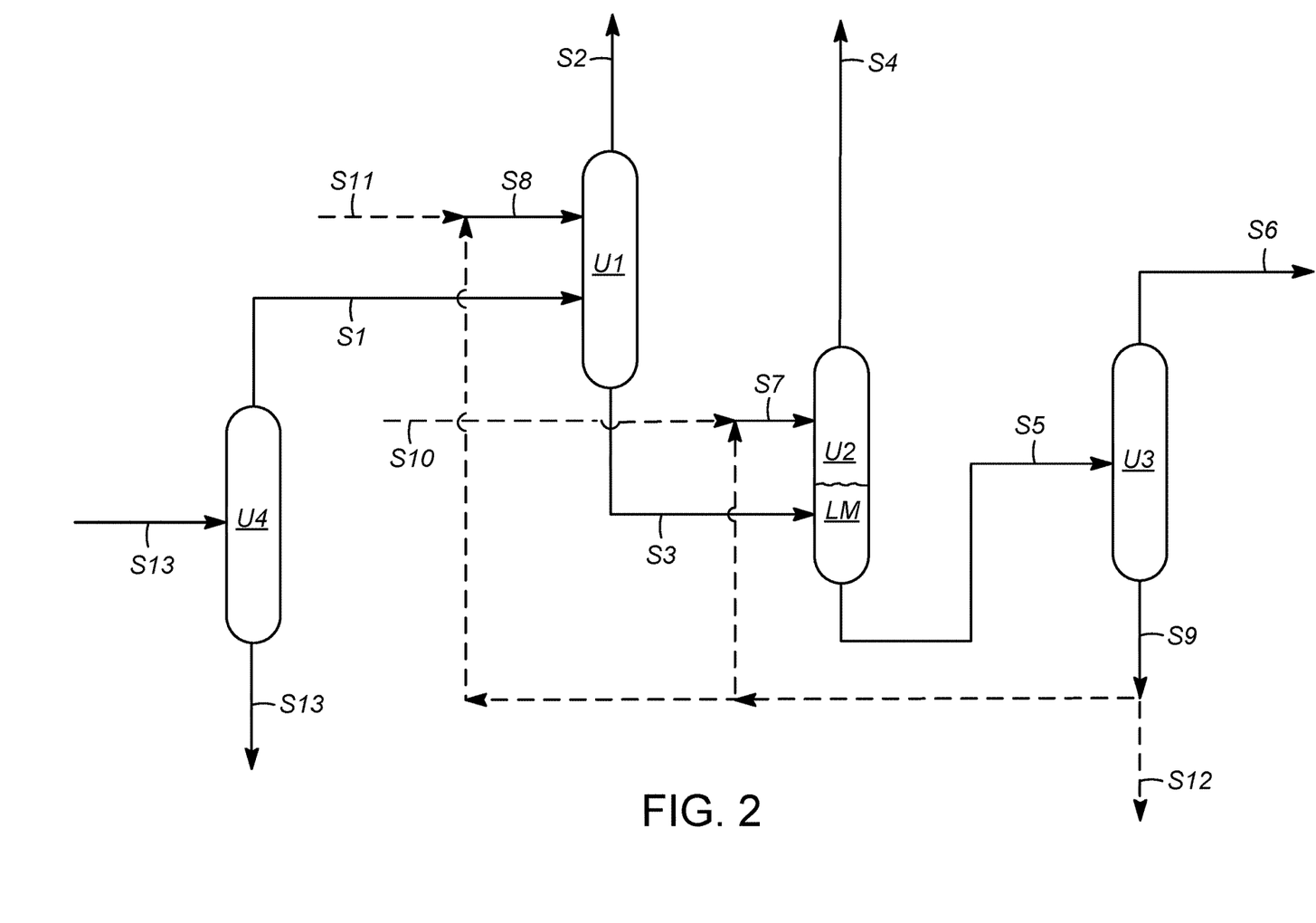
FIG. 2 further illustrates another flow scheme of an extractive distillation process, in which the pretreatment includes a further upstream distillation to remove heavy ($C_9^+$) hydrocarbon components.

According to the alternative embodiment illustrated in FIG. 2, an additional upstream distillation is performed, relative to the embodiment illustrated in FIG. 1. In particular, heavy hydrocarbon-contaminated feed stream (S13) is introduced to heavy removal column (U4) to recover impure feed stream (S1), in this case as an intermediate purity hydrocarbon component. Impure feed stream (S1) is depleted in heavy hydrocarbons (e.g., $C_9+$ hydrocarbons) and enriched in ethylbenzene, one or more of the non-aromatic compounds as described above, and one or more of the further $C_8$ aromatic compounds as described above, relative to heavy hydrocarbon-contaminated feed stream (S13). Heavy removal column (U4) further provides hydrocarbon impurities bottoms fraction (S14), that is enriched in heavy hydrocarbons and depleted in ethylbenzene, one or more of the non-aromatic compounds as described above, and one or more of the further $C_8$ aromatic compounds as described above, relative to heavy hydrocarbon-contaminated feed stream (S13).

The recovered impure feed stream (S1) may then be subjected to an extractive distillation process as described above with respect to the embodiment illustrated in FIG. 1.

In the above description, references to the term "column" mean a vessel in which distillation is performed. References to the term "distillation" mean a separation process that may involve attaining a single stage of vapor-liquid separation (e.g., to achieve a stage of vapor-liquid equilibrium, or to achieve approximately such stage of equilibrium, as the case may be) to resolve an overhead fraction and a bottoms fraction, as in the case of a flash separation. Preferably, however, the distillation may involve attaining multiple stages of vapor-liquid separation to resolve these fractions, optionally with the aid of suitable contacting material or devices, such as trays or packing material (e.g., rings, saddles, etc.), disposed within the column. To enhance the desired separation, the distillation may be further aided with the introduction of a suitable flow gas stream (e.g., an upwardly-flowing gas stream, as in the case of a counter-current stripper column) or a suitable liquid flow stream (e.g., a downwardly-flowing liquid stream, optionally including one or more extractive agent compound(s) of the present invention, as in the case of a counter-current extraction column). References to the terms "overhead fraction" and "bottoms fraction" may mean fractions that are withdrawn from the top and the bottom of a column, respectively. However, these terms are not meant to be limiting in this respect. Rather an "overhead fraction" may otherwise be referred to as a "low-boiling fraction," which is meant to more broadly encompass any fraction having a higher volatility (lower boiling point range) and/or a lower distillation end point temperature, relative to a feed to, and/or relative to a "bottoms fraction" from, the respective distillation column. Likewise, a "bottoms fraction" may otherwise be referred to as a "high-boiling fraction," which is meant to more broadly encompass any fraction having a lower volatility (higher boiling point range) and/or a higher initial boiling point temperature, relative to a feed to, and/or relative to an overhead fraction from, the respective distillation column, with the overhead fraction being as defined above. Initial boiling point and end point temperatures may be determined according to ASTM D86.

References to a first stream or fraction being "enriched in" a given species (e.g., one compound or a class of compounds), relative to a second stream or fraction, mean that the species is present in a higher concentration (e.g., in wt-%) in the first stream compared to that in the second stream. According to particular embodiments, at least 75%, at least 85%, or at least 95%, of the given species, initially present in the second stream, may be recovered into the first stream in which that species is "enriched." According to other particular embodiments, the concentration of that species in the first stream may be at least 75 wt-%, at least 85 wt-%, or at least 95 wt-%. References as to a first stream or fraction being "depleted in" a given species (e.g., one compound or a class of compounds), relative to a second stream or fraction, mean that the species is present in a lower concentration (e.g., in wt-%) in the first stream compared to that in the second stream. According to particular embodiments, at most 25%, at most 15%, or at most 5%, of the given species, initially present in the second stream, may be recovered in the first stream in which that species is "depleted." According to other particular embodiments, the concentration of that species in the first stream may be at most 25 wt-%, at most 15 wt-%, or at most 5 wt-%.

EXAMPLES

The following examples are set forth as representative of the present invention. These examples are not to be construed as limiting the scope of the invention as these and other equivalent embodiments will be apparent in view of the present disclosure and appended claims.

Measurement Methods

Competitive factor (D)—For the determination of the competitive factor, the weight ratios of ethylbenzene to the $C_8$ aromatic compound to be separated are determined from the vapor phase, in equilibrium with liquid mixtures both with and without extractive agent compound(s). Specifically, 1 part of a hydrocarbon composition containing 60 wt-% ethylbenzene and 40 wt-% of the $C_8$ aromatic compound is in one case mixed with 5 parts by weight of the extractive agent compound(s) and in a second case not mixed. In both cases, the respective compositions so obtained are subsequently heated to 80° C. (176° F.). The respective vapor phase compositions, obtained at normal (atmospheric) pressure are analyzed by Gas Chromatography (GC) and the competitive factor (D) is calculated according to the equation:

$$D = \frac{\text{weight ratio ethylbenzene/} C_8 \text{ aromatic compound (with extractive agent)}}{\text{weight ratio ethylbenzene/} C_8 \text{ aromatic compound (without extractive agent)}} \quad \text{(Equation 1)}$$

Hence, competitive factors above a value of 1 show an improvement in the efficiency of the separation, into the vapor phase, of ethylbenzene from the $C_8$ aromatic compound in the mixture, which is attributed to the use of the extractive agent compound(s). Competitive factors below a value of 1 show an improvement in the efficiency of separation, into the liquid phase, of the $C_8$ aromatic compound, which is attributed to the use of the extractive agent compound(s).

Relative Volatility—Relative volatility compares the vapor pressures of two compounds in a binary liquid mixture. Accordingly, it provides an indication of how easy or difficult it is to separate the more volatile compound in the binary mixture from the less volatile compound by distillation. For a liquid binary mixture at a given temperature and a given pressure, the relative volatility α between compounds i and j is calculated according to equation 2:

$$\alpha = \frac{(y_i/x_i)}{(y_j/x_j)} \quad \text{(Equation 2)}$$

wherein α is the relative volatility of the more volatile component i to the less volatile component j; $y_i$ is the vapor-liquid equilibrium molar concentration of component i in the vapor phase; $x_i$ is the vapor-liquid equilibrium molar concentration of component i in the liquid phase; $y_j$ is the vapor-liquid equilibrium molar concentration of component j in the vapor phase; and $x_j$ is the vapor-liquid equilibrium molar concentration of component j in the liquid phase.

Experimental

A) Inventive Example 1 and Comparative Examples 1-10

The competitive factor was determined for a variety of extractive agent compounds according to the method described above. The results are shown in Table 1.

TABLE 1

Table 1:

| | Extractive Agent | Competitive Factor D |
|---|---|---|
| | Comparative Examples (CE) | |
| 1 | 4-Methyloxyacetophenone | 1.015 |
| 2 | Methylsalicylate | 1.016 |
| 3 | Isophorone | 1.030 |
| 4 | 4-Chlorophenol | 1.034 |
| 5 | Nitrobenzol | 1.038 |
| 6 | 1-Decanol | 1.039 |
| 7 | 1-Chloro-2-Nitrobenzene | 1.039 |
| 8 | 3-Chlorophenol | 1.063 |
| 9 | 2,4-Dichlorophenol | 1.087 |
| 10 | 1,2,4-Trichlorobenzene | 1.144 |
| | Inventive Example (IE) | |
| 1 | 1,2-Dichloro-4-nitrobenzene | 1.231 |

As can be seen from these results, 1,2-dichloro-4-nitrobenzene has the highest competitive factor among all of the tested extractive agent compounds. 1,2,4-trichlorobenzene has the highest competitive factor of the Comparative Examples.

B) Comparative and Inventive Examples 2-5

Figure 3:
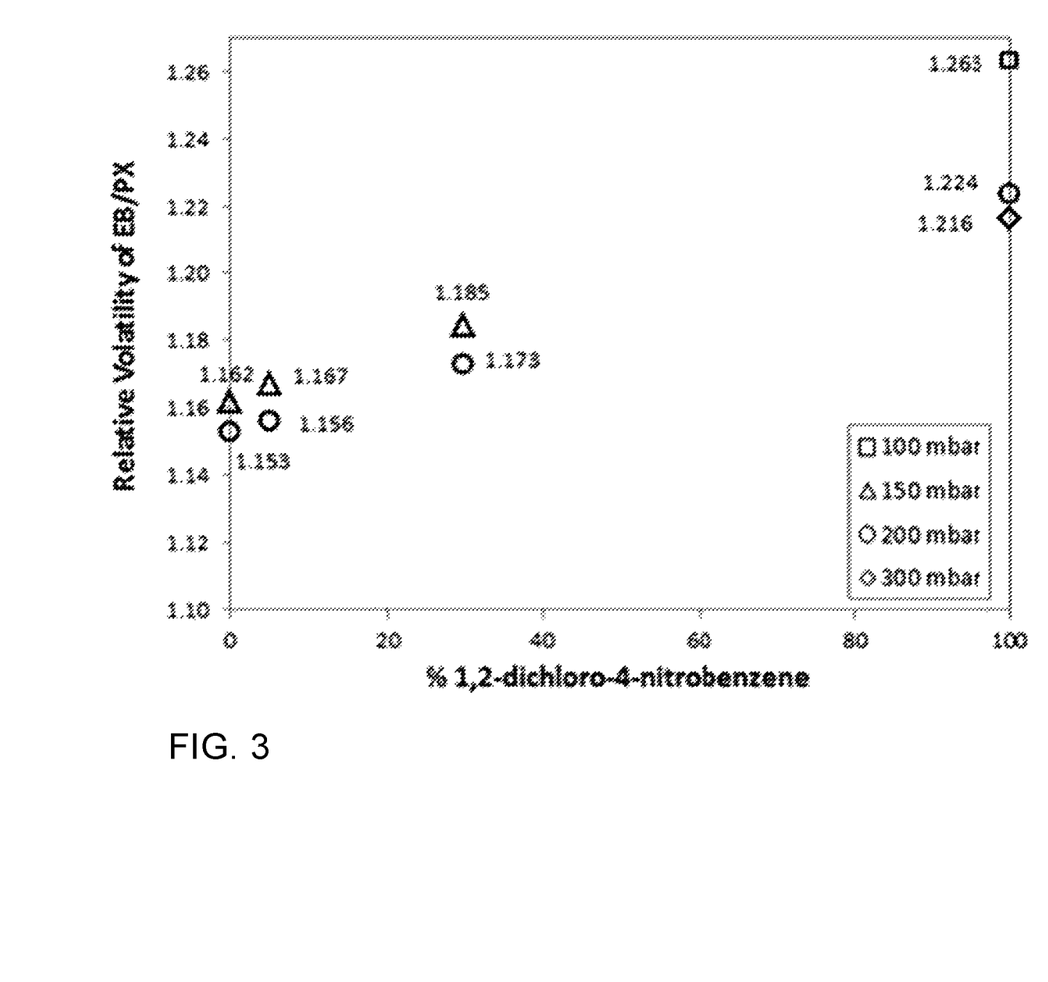
FIG. 3 graphically illustrates the results of relative volatility measurements for ethylbenzene and para-xylene, in different liquid mixtures with 1,2-dichloro-4-nitrobenzene and 1,2,4-trichlorobenzene as an extractive agent compound, used in Examples 2-5, to demonstrate certain advantages of the present invention.

The relative volatility was measured at pressures of 100 millibar (mbar), 150 mbar, 200 mbar, and 300 mbar, according to the procedure described above for various combinations of 1,2-dichloro-4-nitrobenzene and 1,2,4-trichlorobenzene as extractive agent compounds. The hydrocarbon mixture tested in each case contained 60 wt % ethylbenzene and 40 wt % para-xylene, and the weight ratio of extractive agent to hydrocarbon mixture (combined weight of 1,2-dichloro-4-nitrobenzene and 1,2,4-trichlorobenzene to the weight of the hydrocarbon mixture) was 5:1. For this measurement the relative volatility was determined at various pressures using a Fischer® vapor-liquid equilibrium apparatus of ILUDEST Destillationsanlagen GmbH (WaldbUittelbrunn, Germany). The results of these measurements are shown in Table 2 as well as FIG. 3.

TABLE 2

| | Extractive agent | wt.-% | Relative volatility | | | |
|---|---|---|---|---|---|---|
| | | | 100 mbar | 150 mbar | 200 mbar | 300 mbar |
| Example 2 | 1,2-dichloro-4-nitrobenzene | 0 | | 1.162 | 1.153 | |
| | 1,2,4-trichlorobenzene | 100 | | | | |
| Example 3 | 1,2-dichloro-4-nitrobenzene | 5 | | 1.167 | 1.156 | |
| | 1,2,4-trichlorobenzene | 95 | | | | |
| Example 4 | 1,2-dichloro-4-nitrobenzene | 30 | | 1.185 | 1.173 | |
| | 1,2,4-trichlorobenzene | 70 | | | | |
| Example 5 | 1,2-dichloro-4-nitrobenzene | 100 | 1.263 | | 1.224 | 1.216 |
| | 1,2,4-trichlorobenzene | 0 | | | | |

As can be seen from these results, increasing the amount of 1,2-dichloro-4-nitrobenzene, as an extractive agent compound according to the present invention, directionally resulted in increased relative volatility between ethylbenzene and para-xylene. The best result, indicative of the best separation performance between ethylbenzene and para-xylene, was achieved with pure 1,2-dichloro-4-nitrobenzene as the extractive agent compound. Furthermore, decreasing the operating pressure resulted in higher relative volatility and, consequently, improved separation performance between ethylbenzene and para-xylene. Therefore, there is no synergistic effect between 1,2-dichloro-4-nitrobenzene and 1,2,4-trichlorobenzene, in terms of separability. Preferably, therefore, the extractive agent comprises all or substantially all 1,2-dichloro-4-nitrobenzene. Example 2, in which no 1,2-dichloro-4-nitrobenzene was used in the extractive agent, was for comparative purposes.

C) Inventive Example 6

The relative volatility was measured according to the procedure described above for a combinations of 60 wt-% 1,2-dichloro-4-nitrobenzene and 40 wt-% 1,2-dichloro-3-nitrobenzene as extractive agent. The hydrocarbon mixture tested in each case contained 60 wt % ethylbenzene and 40 wt % para-xylene, and the weight ratio of extractive agent to hydrocarbon mixture (combined weight of 1,2-dichloro-4-nitrobenzene and 1,2-dichloro-3-nitrobenzene to the weight of the hydrocarbon mixture) was 5:1. The relative volatility was determined at 100 mbar absolute pressure using a Fischer® vapor-liquid equilibrium apparatus of ILUDEST Destillationsanlagen GmbH (Waldbüttelbrunn, Germany). The results are shown in Table 3.

TABLE 3

| Extractive agent | wt.-% | Relative Volatility, 100 mbar |
|---|---|---|
| Example 6 | 1,2-dichloro-4-nitrobenzene | 60 | 1.221 |
| | 1,2-dichloro-3-nitrobenzene | 40 | |

As can be seen from Inventive Example 6, a mixture of extractive agent compounds according the present invention can provide the advantageous effects of a single extractive agent compound.

D) Inventive Examples 7-14

A hydrocarbon component was prepared for performance evaluation in extractive distillation. The hydrocarbon component was representative of a composition obtained in a para-xylene process flow loop of a commercial para-xylene production process, with such process loop formed from the following streams: (i) a $C_8$ aromatic hydrocarbon stream (or portion thereof), separated as a low-boiling fraction (or overhead fraction) in a xylene column, (ii) a para-xylene-depleted effluent (or portion thereof), separated in a xylene separation zone from the $C_8$ aromatic hydrocarbon stream (or portion thereof), and (iii) a xylene-equilibrated isomerate (or portion thereof), provided from isomerization of the para-xylene-depleted effluent (or portion thereof) in isomerization zone 300. The testing evaluated the ability of extractive distillation to remove ethylbenzene and/or non-aromatic hydrocarbons from such streams of the process loop.

The hydrocarbon component had the composition shown in Table 4.

TABLE 4

| Hydrocarbon Component, species | wt-% | xylene-free basis | Non-aromatic-free basis |
|---|---|---|---|
| n-octane | 2 | 3.08 | |
| ethylcyclohexane | 2 | 3.08 | |
| cyclooctane | 2 | 3.08 | |
| ethylbenzene | 59 | 90.77 | 62.77 |
| para-xylene | 11 | | 11.70 |
| meta-xylene | 11 | | 11.70 |
| ortho-xylene | 13 | | 13.83 |

As extractive agents, mixtures of the extractive agent compounds (i) 3,4-dichloroaniline (34DCA, boiling point=263° C. or 505° F.) and (ii) 1,2-dichloro-4-nitrobenzene (DCNB, boiling point=273° C. or 523° F.) were prepared at mixing ratios of (A) 25/75 w/w (i):(ii), (B) 50/50 w/w of (i):(ii), and (C) 75/25 w/w of (i):(ii). As further extractive agents, these compounds were used in their pure form (i.e., (D), 0/100 w/w (i):(ii) for pure DCNB and (E) 100/0 w/w (i):(ii) for pure 34DCA).

To determine the ease of separability of the various species of the hydrocarbon component, the competitive factor was determined for the extractive agents, using the procedure and calculation described above, except that the vapor-liquid equilibrium data were obtained for (i) 1 part of the hydrocarbon component, mixed with 3 parts of the extractive agent by weight, and (ii) the hydrocarbon component alone. Also, these data were obtained at a temperature of 70° C. (158° F.), following equilibration for 12 hours. The competitive factors of ethylbenzene with respect to para-xylene, meta-xylene, and ortho-xylene, determined for certain extractive agents, as well as the standard deviation of the measurements for each determination, are shown in Table 5 as well as FIG. 4, in which the given percentages are by weight.

TABLE 5

| | | ethylbenzene/ para-xylene | | ethylbenzene/ meta-xylene | | ethylbenzene/ ortho-xylene | |
|---|---|---|---|---|---|---|---|
| | Extractive Agent | Competitive Factor, D | Std. Dev. | Competitive Factor, D | Std. Dev. | Competitive Factor, D | Std. Dev. |
| Example 7 | 100% DCNB | 1.1330 | 0.0085 | 1.1271 | 0.0190 | 1.3085 | 0.0191 |
| Example 8 | 25% 34DCA/ 75% DCNB | 1.0910 | 0.0134 | 1.1347 | 0.0218 | 1.2515 | 0.0025 |
| Example 9 | 75% 34DCA/ 25% DCNB | 1.0394 | 0.0133 | 1.0815 | 0.0167 | 1.2156 | 0.0127 |
| Example 10 | 100% 34DCA | 1.0051 | 0.0156 | 1.0530 | 0.0232 | 1.1730 | 0.0121 |

Figure 5:
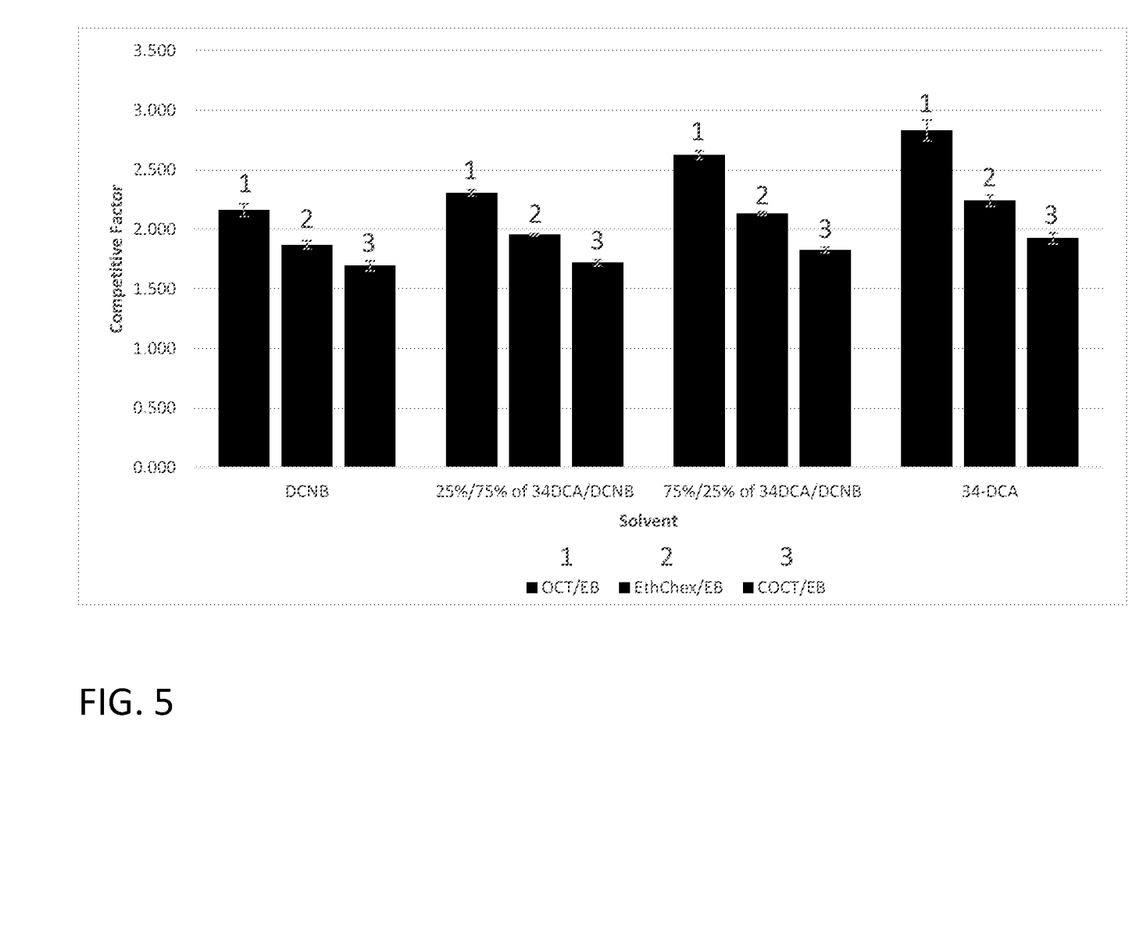
FIG. 5 graphically illustrates the competitive factor of the non-aromatic hydrocarbons, n-octane, ethylcyclohexane, and cyclooctane, with respect to ethylbenzene, obtained for mixtures of two extractive agent compounds, namely 1,2-dichloro-4-nitrobenzene and 3,4 dichloroaniline.

The competitive factors of the non-aromatic hydrocarbons n-octane, ethylcyclohexane, and cyclooctane with respect to ethylbenzene, determined for these extractive agents, as well as the standard deviation of the measurements for each determination, are shown in Table 6 as well as FIG. 5, in which the given percentages are by weight.

TABLE 6

|  | Extractive Agent | n-octane/ ethylbenzene | | ethylcyclohexane/ ethylbenzene | | cyclooctane/ ethylbenzene | |
| --- | --- | --- | --- | --- | --- | --- | --- |
|  |  | Competitive Factor, D | Std. Dev. | Competitive Factor, D | Std. Dev. | Competitive Factor, D | Std. Dev. |
| Example 11 | 100% DCNB | 2.1611 | 0.0542 | 1.8680 | 0.0337 | 1.6933 | 0.0418 |
| Example 12 | 25% 34DCA/ 75% DCNB | 2.3059 | 0.0264 | 1.9539 | 0.0086 | 1.7198 | 0.0256 |
| Example 13 | 75% 34DCA/ 25% DCNB | 2.6237 | 0.0377 | 2.1322 | 0.0132 | 1.8267 | 0.0240 |
| Example 14 | 100% 34DCA | 2.8305 | 0.0878 | 2.2401 | 0.0475 | 1.9252 | 0.0469 |

Figure 4:
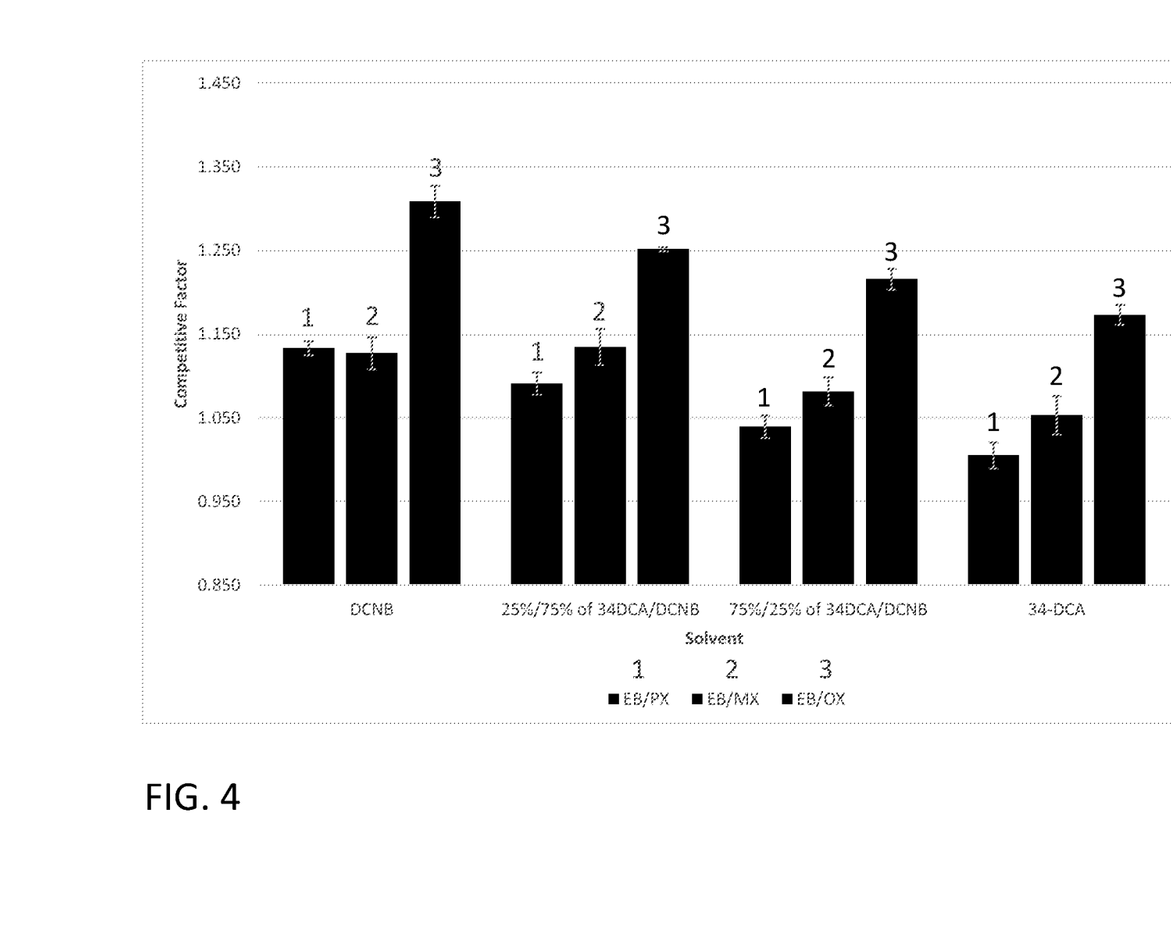
FIG. 4 graphically illustrates the competitive factor of ethylbenzene with respect to para-xylene, meta-xylene, and ortho-xylene, obtained for mixtures of two extractive agent compounds, namely 1,2-dichloro-4-nitrobenzene and 3,4 dichloroaniline.

As shown in Tables 5 and 6, as well as in the corresponding FIGS. 4 and 5, all of the extractive agents tested had the ability to improve the efficiency of separation of both ethylbenzene and non-aromatic hydrocarbons into a vapor phase, by distillation of the hydrocarbon component in liquid mixtures with these extractive agents.

E) Inventive Examples 15-21

Vapor-liquid equilibrium data at pressures of 100 mbar, 150 mbar, 200 mbar, and 300 mbar were obtained for liquid mixtures using a flash separation model with Aspen Plus® simulation software. The liquid mixtures that were modeled were namely mixtures of (i) a hydrocarbon component, having a composition of 60 wt-% ethylbenzene, 10 wt-% para-xylene, 20 wt-% meta-xylene, and 10 wt-% ortho-xylene, and (ii) an extractive agent, with the weight ratio of the extractive agent to hydrocarbon component being 3:1. The extractive agents that were modeled were mixtures of the extractive agent compounds (i) 3,4-dichloroaniline (34DCA) and (ii) 1,2-dichloro-4-nitrobenzene (DCNB) at mixing ratios of (A) 5/95 w/w (i):(ii); 25/75 w/w (i):(ii), (B) 50/50 w/w of (i):(ii), (C) 75/25 w/w of (i):(ii), and 95/5 w/w of (i):(ii). As further extractive agents, these compounds were used in their pure form (i.e., (D), 0/100 w/w (i):(ii) for pure DCNB and (E) 100/0 w/w (i):(ii) for pure 34DCA). The raw, flash vapor and liquid equilibrium concentrations of the various species of the hydrocarbon component were used to calculate relative volatilities between ethylbenzene in each of the xylene isomers. These relative volatilities at each pressure simulated, and for each liquid mixture formed using the various extractive agents described above, are shown in Table 7.

TABLE 7

|  | Extractive Agents | Pressure (mbar) | $\alpha_{EB/PX}$ | $\alpha_{EB/MX}$ | $\alpha_{EB/OX}$ |
| --- | --- | --- | --- | --- | --- |
| Example 15 | 100% DCNB | 100 | 1.426 | 1.470 | 1.741 |
|  |  | 150 | 1.399 | 1.439 | 1.689 |
|  |  | 200 | 1.380 | 1.417 | 1.653 |
|  |  | 300 | 1.354 | 1.386 | 1.604 |
| Example 16 | 5% 34 DCA 95% DCNB | 100 | 1.415 | 1.459 | 1.727 |
|  |  | 150 | 1.388 | 1.428 | 1.676 |
|  |  | 200 | 1.370 | 1.406 | 1.641 |
|  |  | 300 | 1.344 | 1.376 | 1.592 |

TABLE 7-continued

|  | Extractive Agents | Pressure (mbar) | $\alpha_{EB/PX}$ | $\alpha_{EB/MX}$ | $\alpha_{EB/OX}$ |
| --- | --- | --- | --- | --- | --- |
| Example 17 | 25% 34 DCA 75% DCNB | 100 | 1.366 | 1.409 | 1.668 |
|  |  | 150 | 1.343 | 1.381 | 1.621 |
|  |  | 200 | 1.326 | 1.361 | 1.589 |
|  |  | 300 | 1.303 | 1.334 | 1.544 |
| Example 18 | 50% 34 DCA 50% DCNB | 100 | 1.299 | 1.340 | 1.587 |
|  |  | 150 | 1.279 | 1.316 | 1.545 |
|  |  | 200 | 1.265 | 1.299 | 1.516 |
|  |  | 300 | 1.246 | 1.275 | 1.476 |
| Example 19 | 75% 34 DCA 25% DCNB | 100 | 1.226 | 1.265 | 1.498 |
|  |  | 150 | 1.211 | 1.245 | 1.462 |
|  |  | 200 | 1.200 | 1.231 | 1.437 |
|  |  | 300 | 1.184 | 1.212 | 1.403 |
| Example 20 | 95% 34 DCA 5% DCNB | 100 | 1.153 | 1.193 | 1.412 |
|  |  | 150 | 1.144 | 1.179 | 1.383 |
|  |  | 200 | 1.132 | 1.164 | 1.358 |
|  |  | 300 | 1.133 | 1.159 | 1.341 |
| Example 21 | 100% DCA | 100 | 1.149 | 1.185 | 1.403 |
|  |  | 150 | 1.138 | 1.170 | 1.373 |
|  |  | 200 | 1.130 | 1.159 | 1.352 |
|  |  | 300 | 1.119 | 1.145 | 1.324 |

From this data, it can be seen that favorable increases in relative volatility between ethylbenzene and other $C_8$ aromatic hydrocarbons can be obtained using extractive agent compounds as described herein, and particularly those having Formula (I) as described above, with dichloroaniline and dichloronitrobenzene and their mixtures being exemplary extractive agents.

Overall, aspects of the invention are directed to improved processes for the separation of ethylbenzene from a hydrocarbon component comprising ethylbenzene and at least one other $C_8$ aromatic compound, using one or more distillation steps with the optional recycle of an extractive agent compound that is used to facilitate this separation. Those having skill in the art, with the knowledge gained from the present disclosure, will recognize that various changes can be made to the disclosed extractive distillation processes in attaining these and other advantages, without departing from the scope of the present invention. Accordingly, it should be understood that the features described herein are susceptible to changes or substitutions. The specific embodiments illustrated and described herein are for illustrative purposes only, and not limiting of the invention as set forth in the appended claims.

What is claimed is:

1. An extractive distillation process, the process comprising (a) distilling a liquid mixture comprising ethylbenzene, at least one further $C_8$ aromatic compound, and an extractive agent compound,
wherein the extractive agent compound includes a carbocyclic or heterocyclic ring structure, said ring structure being substituted with at least one $NR^aR^b$-group radical and at least two halo radicals, and
wherein $R^a$ and $R^b$ are independently selected from the group consisting of an oxygen radical, a hydrogen radical, and a hydrocarbyl radical having from about 1 to about 20 carbon atoms.

2. The process of claim 1, wherein the extractive agent compound includes a carbocyclic ring structure that is an aromatic ring structure.

3. The process of claim 2, wherein the extractive agent compound is an aromatic compound of Formula (I):

(I)

wherein $R^a$ and $R^b$ are as defined in claim 1, and
wherein $R^2$-$R^6$ are independently selected from the group consisting of halo, a hydrogen radical, and a hydrocarbyl radical having from about 1 to about 20 carbon atoms, and further wherein at least two of $R^2$-$R^6$ are halo.

4. The process of claim 3, wherein, in Formula (I), said at least two of $R^2$-$R^6$ are chloro.

5. The process of claim 3, wherein, in Formula (I), at least $R^3$ and $R^4$ are halo.

6. The process of claim 5, wherein, in Formula (I), $R^2$, $R^5$, and $R^6$ are independently selected from the group consisting of a hydrogen radical and a hydrocarbyl radical having from about 1 to about 20 carbon atoms.

7. The process of claim 3, wherein, in Formula (I), $R^2$ and $R^3$ are halo.

8. The process of claim 7, wherein, in Formula (I), $R^4$, $R^5$, and $R^6$ are independently selected from the group consisting of a hydrogen radical and a hydrocarbyl radical having from about 1 to about 20 carbon atoms.

9. The process of claim 1, wherein, in Formula (I), $R^a$ and $R^b$ are both oxygen radicals, whereby the $NR^aR^b$-group radical is nitro.

10. The process of claim 1, wherein the extractive agent compound is an isomer of dichloronitrobenzene.

11. The process of claim 1, wherein the extractive agent compound is 1,2-dichloro-3-nitrobenzene or 1,2-dichloro-4-nitrobenzene.

12. The process of claim 1, wherein the liquid mixture comprises both 1,2-dichloro-3-nitrobenzene and 1,2-dichloro-4-nitrobenzene.

13. The process of claim 1, wherein, in Formula (I), $R^a$ and $R^b$ are both hydrogen radicals, whereby the $NR^aR^b$-group radical is amino.

14. The process claim 1, wherein the extractive agent compound is an isomer of dichloroaniline.

15. The process of claim 1, wherein the extractive agent compound is 3,4-dichloroaniline.

16. The process of claim 1, wherein the liquid mixture comprises both an isomer of dichloronitrobenzene and an isomer of dichloroaniline.

17. The process of claim 1, wherein the liquid mixture comprises (i) 3,4-dichloroaniline and (ii) 1,2-dichloro-4-nitrobenzene or 1,2-dichloro-3-nitrobenzene.

18. A liquid mixture comprising ethylbenzene, at least one further $C_8$ aromatic compound, and an extractive agent compound, wherein the extractive agent compound is present in the liquid mixture in an amount such that the relative volatility (a) between the ethylbenzene and the at least one further $C_8$ aromatic compound is at least about 1.14 at 200 millibar (mbar),
wherein the extractive agent compound includes a carbocyclic or heterocyclic ring structure, said ring structure being substituted with at least one $NR^aR^b$-group radical and at least two halo radicals, and wherein $R^a$ and $R^b$ are independently selected from the group consisting of an oxygen radical, a hydrogen radical, and a hydrocarbyl radical having from about 1 to about 20 carbon atoms.

19. An extractive distillation process comprising:
(a) distilling a liquid mixture of a purified feed stream and an extractive agent compound to provide (i) an overhead fraction enriched in ethylbenzene, relative to the liquid mixture, and (ii) a bottoms fraction that, relative to the liquid mixture, is enriched in both the at least one further $C_8$ aromatic compound and the extractive agent compound, and is depleted in ethylbenzene;
(b) distilling the bottoms fraction to provide (i) a second bottoms fraction enriched in the extractive agent compound, relative to the bottoms fraction, and (ii) a second overhead fraction enriched in the at least one further $C_8$ aromatic compound, relative to the bottoms fraction; and
(c) recycling at least a portion of the second bottoms fraction to provide at least a portion of the extractive agent compound in the liquid mixture in step (a),
wherein the extractive agent compound includes a carbocyclic or heterocyclic ring structure, said ring structure being substituted with at least one $NR^aR^b$-group radical and at least two halo radicals, and wherein $R^a$ and $R^b$ are independently selected from the group consisting of an oxygen radical, a hydrogen radical, and a hydrocarbyl radical having from about 1 to about 20 carbon atoms.

20. The process of claim 19, further comprising, prior to step (a),
recovering, as a bottoms fraction from an upstream distillation of an impure feed stream, the purified feed steam comprising ethylbenzene and at least one further $C_8$ aromatic compound, wherein the purified feed stream is depleted in non-aromatic hydrocarbons, relative to the impure feed stream.

* * * * *